US012570946B2

(12) United States Patent
Kouge et al.

(10) Patent No.: US 12,570,946 B2
(45) Date of Patent: Mar. 10, 2026

(54) SENSOR UNIT AND CELL CULTURE ANALYSIS DEVICE HAVING SAME

(71) Applicant: PHC Holdings Corporation, Tokyo (JP)

(72) Inventors: Masahiro Kouge, Ehime (JP); Takumi Shima, Ehime (JP); Masato Nishiyama, Saitama (JP); Kouji Watanabe, Ehime (JP); Masaki Yamamoto, Ehime (JP); Kenta Nakamae, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 592 days.

(21) Appl. No.: 18/103,990

(22) Filed: Jan. 31, 2023

(65) Prior Publication Data

US 2023/0167396 A1 Jun. 1, 2023

Related U.S. Application Data

(63) Continuation of application No. PCT/JP2021/040117, filed on Oct. 29, 2021.

(30) Foreign Application Priority Data

Nov. 6, 2020 (JP) ................................. 2020-185614
Jan. 15, 2021 (JP) ................................. 2021-004694

(51) Int. Cl.
C12M 1/34 (2006.01)
(52) U.S. Cl.
CPC .................................. *C12M 41/30* (2013.01)

(58) Field of Classification Search
CPC ....... C12M 41/30; C12M 41/48; C12M 23/12
USPC ...................................................... 435/287.1
See application file for complete search history.

(56) References Cited

U.S. PATENT DOCUMENTS

| | | | |
|---|---|---|---|
| 7,382,531 B2 | 6/2008 | Tsuchiya et al. |
| 8,455,241 B2 | 6/2013 | Osawa et al. |
| 9,170,255 B2 | 10/2015 | Teich et al. |
| 10,597,623 B2 | 3/2020 | Song et al. |
| 11,946,035 B2 | 4/2024 | Ludlam et al. |

(Continued)

FOREIGN PATENT DOCUMENTS

| | | |
|---|---|---|
| JP | 2004-113092 A | 4/2004 |
| JP | 2006-126481 A | 5/2006 |

(Continued)

OTHER PUBLICATIONS

International Search Report dated Dec. 28, 2021 issued in International Patent Application No. PCT/JP2021/040117, with English translation.

(Continued)

*Primary Examiner* — Michael L Hobbs
*Assistant Examiner* — Lenora A Abel
(74) *Attorney, Agent, or Firm* — Rimon P.C.

(57) ABSTRACT

A sensor unit has sensors for measuring the components of a culture medium in a culture vessel, and comprises a plurality of sensors and a linking portion. The plurality of sensors each have a main body and a sensing unit disposed on the lower end side of the main body and immersed in the culture medium to measure the components of the culture medium. The linking portion links the plurality of sensors on the upper end side of the main body.

17 Claims, 41 Drawing Sheets

(56) References Cited

U.S. PATENT DOCUMENTS

| | | | |
|---|---|---|---|
| 2006/0092506 A1 | 5/2006 | Tsuchiya et al. | |
| 2009/0269841 A1* | 10/2009 | Wojciechowski | ..... C12M 29/18 |
| | | | 435/303.1 |
| 2009/0325280 A1 | 12/2009 | Osawa et al. | |
| 2016/0096173 A1* | 4/2016 | Teich | .................... B01L 3/5085 |
| | | | 435/288.4 |
| 2017/0002307 A1 | 1/2017 | Ikefuji | |
| 2018/0142196 A1 | 5/2018 | Coppeta et al. | |
| 2021/0002602 A1 | 1/2021 | Ludlam et al. | |
| 2022/0365020 A1 | 11/2022 | Nakamae et al. | |

FOREIGN PATENT DOCUMENTS

| | | |
|---|---|---|
| JP | 2007-505316 A | 3/2007 |
| JP | 2011-092117 A | 5/2011 |
| JP | 2014-128290 A | 7/2014 |
| JP | 2018-170977 A | 11/2018 |
| JP | 2021-065124 A | 4/2021 |
| JP | 2021-153410 A | 10/2021 |
| WO | 2015/136794 A1 | 9/2015 |
| WO | 2018/213357 A1 | 11/2018 |
| WO | 2019/222333 A1 | 11/2019 |
| WO | 2021/079892 A1 | 4/2021 |

OTHER PUBLICATIONS

Notice of Reasons for Refusal issued in corresponding JP Application No. 2021-004694, dated Jan. 23, 2024 w/ English MT.

Extended European Search Report dated May 24, 2024 issued in the corresponding European Patent Application No. 21889137.2.

* cited by examiner

SENSOR UNIT AND CELL CULTURE ANALYSIS DEVICE HAVING SAME

CROSS-REFERENCE OF RELATED APPLICATIONS

This application is a Continuation of International Patent Application No. PCT/JP2021/040117, filed on Oct. 29, 2021, which in turn claims the benefit of Japanese Patent Application No. 2020-185614, filed on Nov. 6, 2020, and Japanese Patent Application No. 2021-004694, filed on Jan. 15, 2021, the entire disclosures of which Applications are incorporated by reference herein.

TECHNICAL FIELD

The present invention relates to a sensor unit used in cell culture analysis, and to a cell culture analysis device equipped with this sensor unit.

BACKGROUND ART

In the configuration of a conventional cell culture analysis device, a sensor is fixed in a through-hole portion provided to a board, and a lead wire for taking off signals is connected to the sensor.

For example, Patent Literature 1 discloses a cell culture analysis device having a cartridge that mates with a plate provided with a plurality of cell culture vessels.

This cell culture analysis device has sensors for measuring inside each culture vessel, a plurality of openings into which these sensors are inserted are provided to the cartridge, and the sensors and fiber cables are connected inside the openings. These fiber cables are connected to an external control unit.

CITATION LIST

Patent Literature

Patent Literature 1: U.S. Pat. No. 9,170,255

SUMMARY

However, the following problems are encountered with the above-mentioned conventional cell culture analysis device.

With the cell culture analysis device disclosed in the above publication, since the sensors inserted into the culture vessels were provided individually, it was difficult to accurately position each sensor with respect to the culture vessel.

Therefore, there was a risk of variance in the immersion depth, etc., of the sensors in the culture medium placed in the culture vessel, which decreased measurement accuracy.

Technical Problem

It is an object of the present invention to provide a sensor unit with which the positional accuracy of sensors with respect to the culture vessel can be improved, as well as a cell culture analysis device comprising this sensor unit.

Solution to Problem

The sensor unit according to the present invention is a sensor unit having sensors for measuring the components of a culture medium in a culture vessel, and comprises a plurality of sensors and a linking portion. The plurality of sensors each have a main body and a sensing unit that is disposed on the lower end side of the main body and is immersed in the culture medium to measure the components of the culture medium. The linking portion links the plurality of sensors on the upper end side of the main body.

Effects

With the sensor unit of the present invention, the positional accuracy of the sensors with respect to the culture vessel can be improved.

DESCRIPTION OF THE EMBODIMENTS

Embodiment 1

The cell culture analysis device 1 including a sensor unit 27 according to an embodiment of the present invention will now be described with reference to the appended drawings.
Overview of Cell Culture Analysis Device 1

Figure 1:
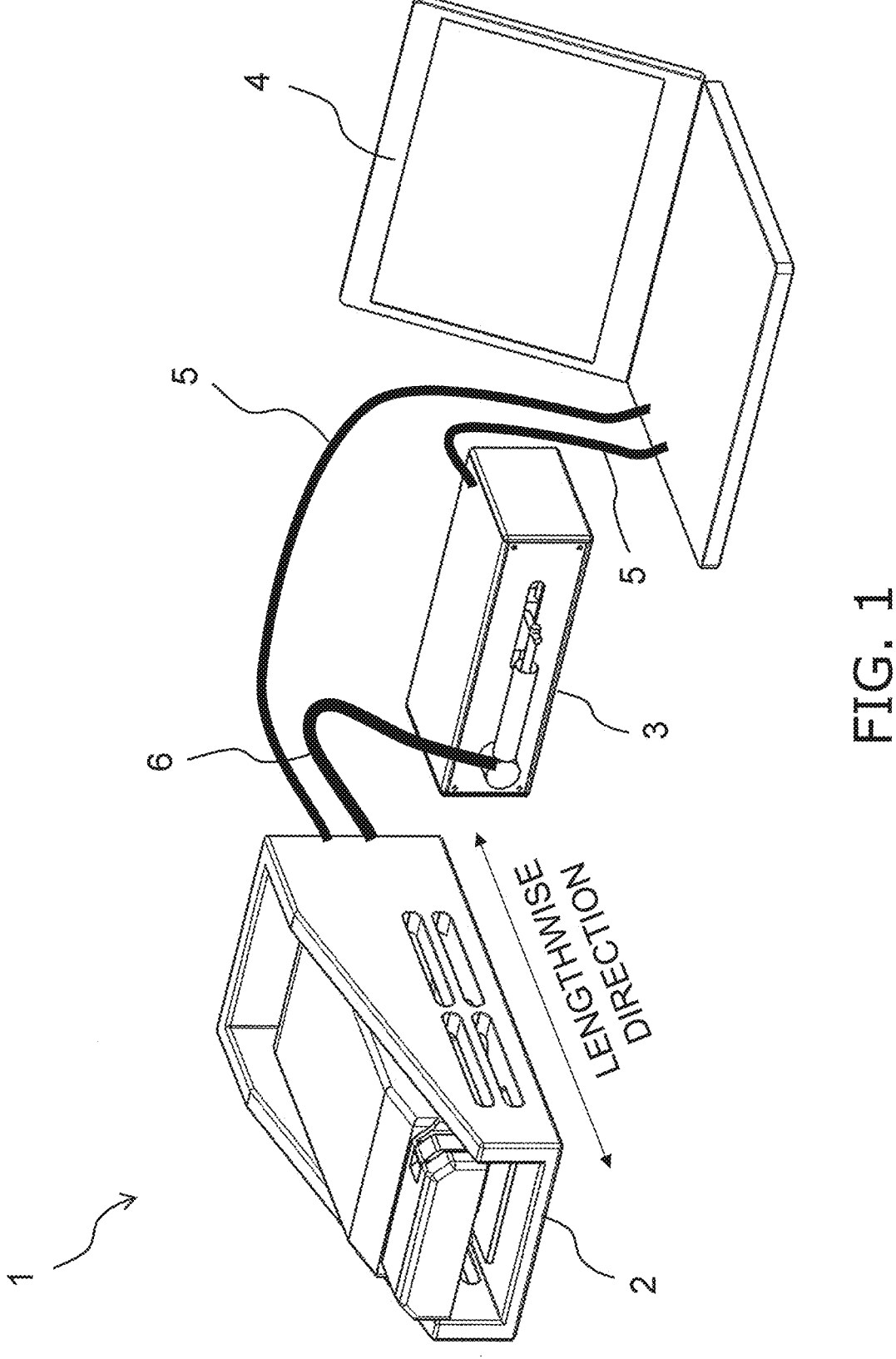
FIG. 1 is a diagram of the configuration of the cell culture analysis device according to an embodiment of the present invention.

FIG. 1 shows the configuration of the cell culture analysis device 1.

The cell culture analysis device 1 electrochemically senses the concentration of a specific component contained in a culture medium in a state in which a portion of a sensor 43 (see FIG. 14, etc.) is immersed in the culture medium (liquid) contained in a well (culture vessel) 25*a* (see FIG. 12), and comprises an analysis unit 2, a drive unit 3 serving as an air pressure supply unit, and a control unit 4 that controls the analysis unit 2 and the drive unit 3. The control unit 4, the analysis unit 2, and the drive unit 3 are connected by an electrical cable 5. The drive unit 3 and the analysis unit 2 are connected by a piping tube 6.

Figure 2:
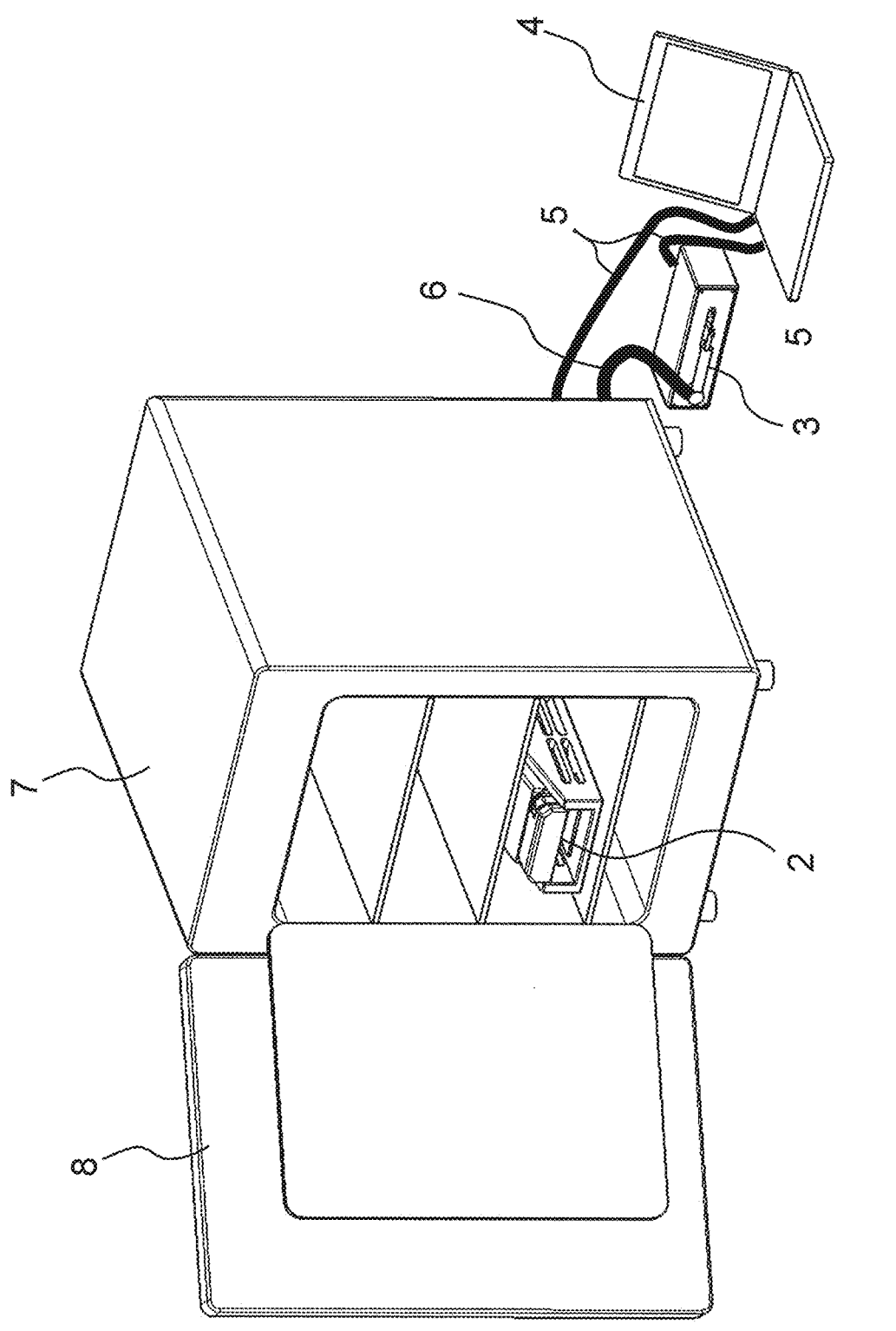
FIG. 2 is a diagram showing a state in which the analysis unit of the cell culture analysis device in FIG. 1 is installed in a culture incubator.

FIG. 2 shows a usage example of the cell culture analysis device 1 disposed in a culture incubator 7.

The analysis unit 2 of the cell culture analysis device 1 is disposed inside the culture incubator 7. The control unit 4 connected to the analysis unit 2 by the electrical cable 5 and the drive unit 3 connected to the analysis unit 2 by the piping tube 6 are disposed outside the culture incubator 7.

This allows the user to analyze the culture state inside the culture incubator 7 via the control unit 4, without having to open and close the door 8 of the culture incubator 7. That is, air contamination due to contamination inside the culture incubator 7 can be prevented when analyzing the culture state.

Figures 3A, 3B:
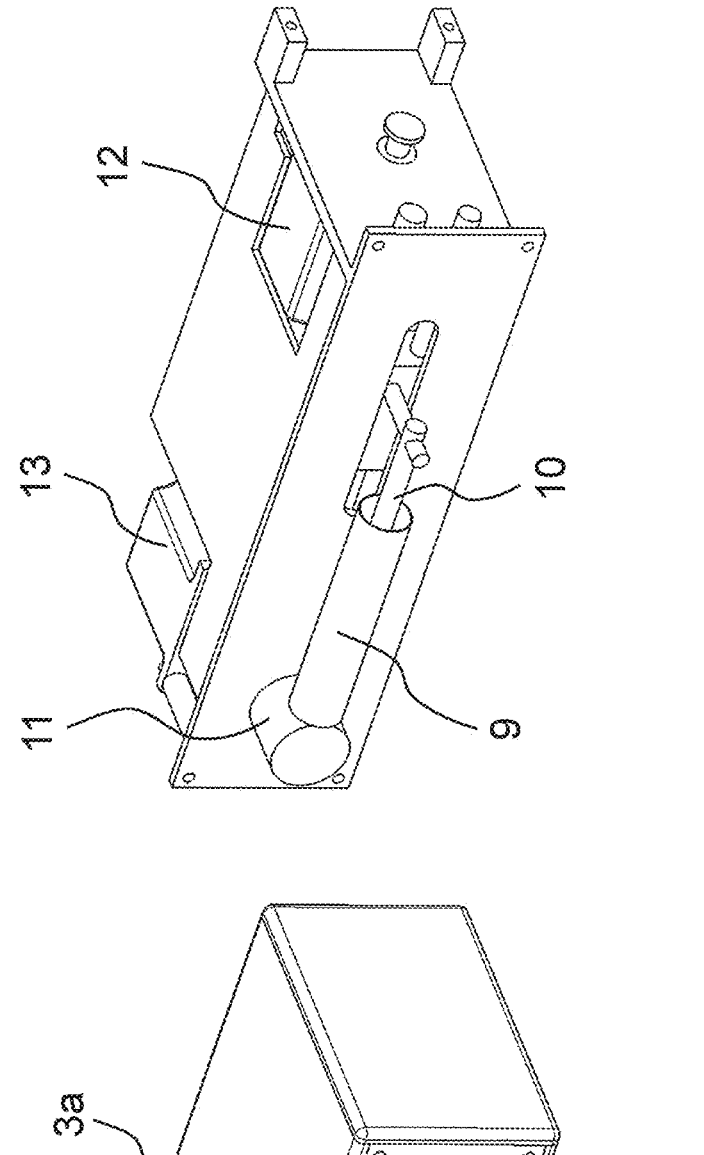
FIGS. 3A and 3B are diagrams of the configuration of a drive unit included in the cell culture analysis device in FIG. 1.

FIGS. 3A and 3B show the configuration of the drive unit 3.

The drive unit 3 is an air pressure supply unit for the analysis unit 2, and as shown in FIGS. 3A and 3B, has a syringe 9, a plunger 10, a multi-way switching valve 11, a plunger motor 12, and a valve motor 13. Air pressure is adjusted by compressing or drawing out air in the syringe 9 with the plunger 10. The plunger 10 is linked to the multi-way switching valve 11.

The plunger motor 12 and the motor 13 for the multi-way switching valve 11 are disposed in a housing 3*a* of the drive unit 3. These motors 12 and 13 are controlled by the control unit 4, which is connected via the electrical cable 5.

Figure 4:
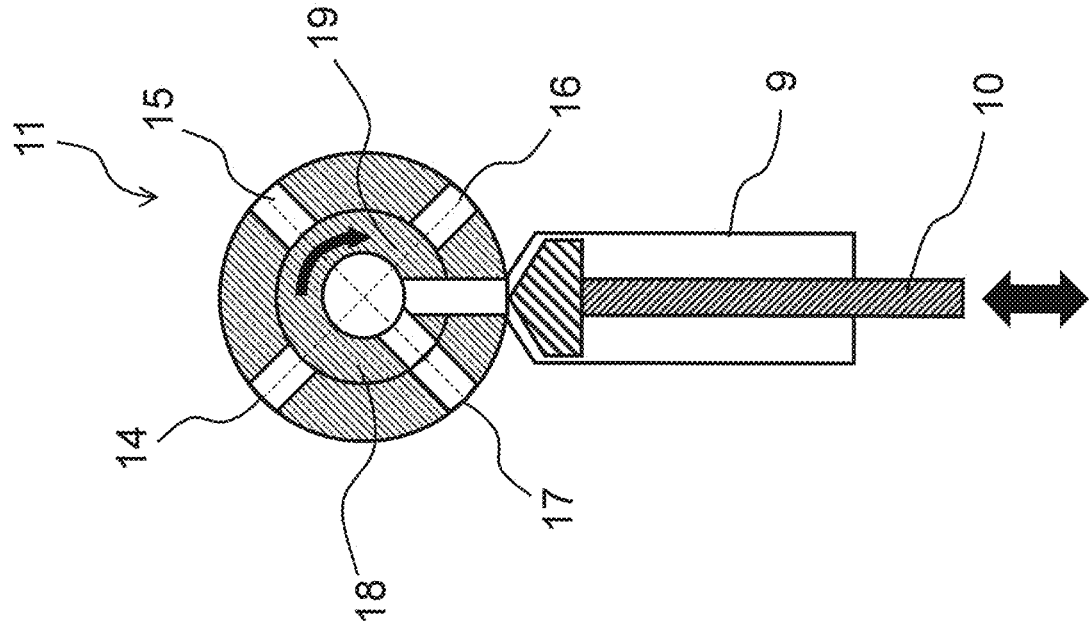
FIG. 4 is a cross-sectional view of the configuration of a multi-way switch valve included in the drive unit of FIG. 3A.

FIG. 4 shows the configuration of the multi-way switching valve 11 included in the drive unit 3.

The multi-way switching valve 11 has a valve 14 for an additive addition unit A, a valve 15 for an additive addition unit B, and a stirring member valve 16, as valves of the air supply system for the analysis unit 2.

The multi-way switching valve 11 has the stirring member valve 16 and an intake valve 17, as intake system valves for the analysis unit 2.

The multi-way switching valve 11 is controlled so as to control the rotation of the rotating part 18 to determine the position of a rotating flow path 19 in the peripheral direction, connect a specific valve and the syringe 9, and supply air pressure.

More specifically, air blown toward the analysis unit 2 first controls the rotation of a rotating part 18 to connect the flow paths of the air intake valve 17 and the syringe 9. The plunger 10 is then pulled in the suction direction to draw air into the syringe 9 through the intake valve 17. Next, the rotation of the rotating part 18 is controlled to connect the flow path of the syringe 9 to the specific valves 14, 15, and 16 of the gas supply system, and then the plunger 10 is depressed in the compression direction, causing air to be supplied to the specific valves 14, 15, and 16.

Figure 5:
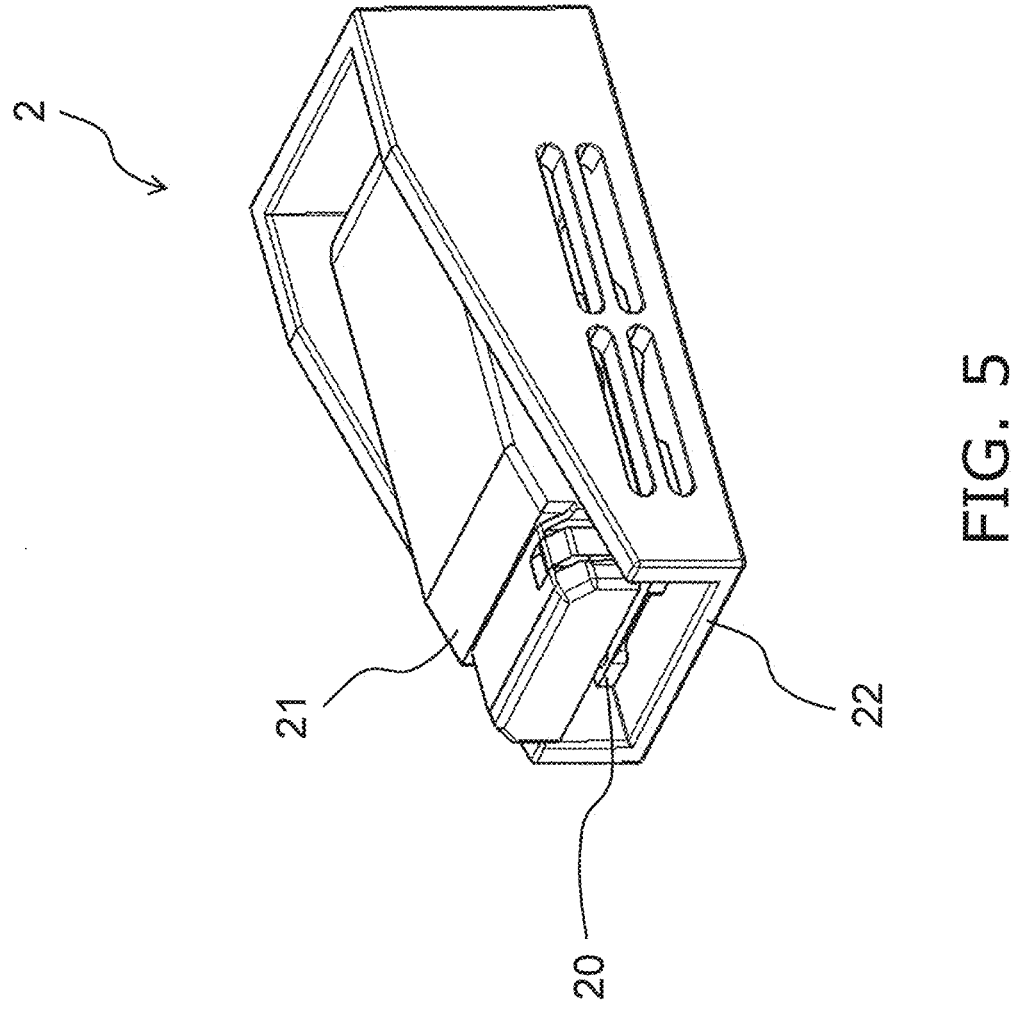
FIG. 5 is a diagram of the configuration of the analysis unit included in the cell culture analysis device in FIG. 1.

FIG. 5 shows the configuration of the analysis unit 2.

The analysis unit 2 is designed to be shorter in the horizontal direction, lower in the height direction, and longer in the depth direction so that a plurality of units can be installed in the culture incubator. This is because the culture space of a typical culture incubator is longer in the depth direction and lower in the height direction, and has a shape that matches this.

The analysis unit 2 has an adapter unit 20, a top unit 21, and a bottom unit 22, and is configured such that the adapter unit 20 is sandwiched between the top unit 21 and the bottom unit 22.

Figure 6:
FIG. 6 is a diagram showing a state in which an adapter unit constituting the analysis unit in FIG. 5 is attached between a top unit and a bottom unit.

As shown in FIG. 6, the adapter unit 20 is attached by being slid through a front opening 23 formed between the top unit 21 and the bottom unit 22. As a result, the height of the analysis unit 2 can be kept lower.

Also, as shown in FIG. 6, the adapter unit 20 consists of an adapter bottom 24, a well plate 25, an adapter top 26, and a sensor unit 27, in that order starting from the bottom.

Figure 7B:
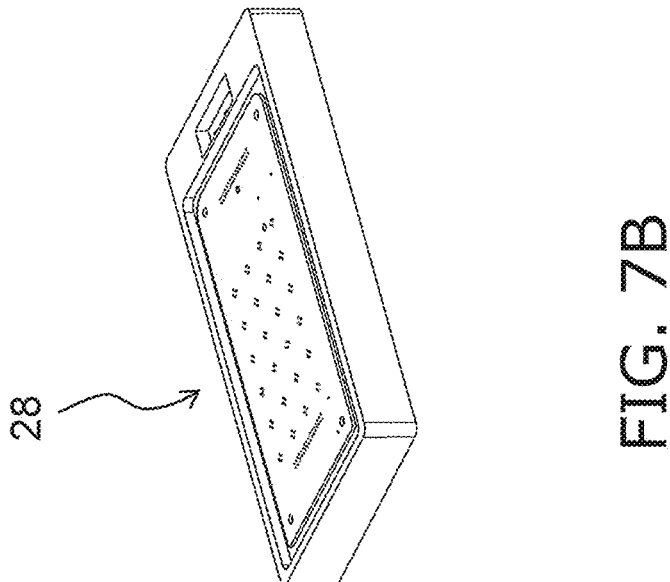
FIG. 7B is a diagram of the configuration of a board unit installed in the analysis unit in FIG. 7A.
Figure 7A:
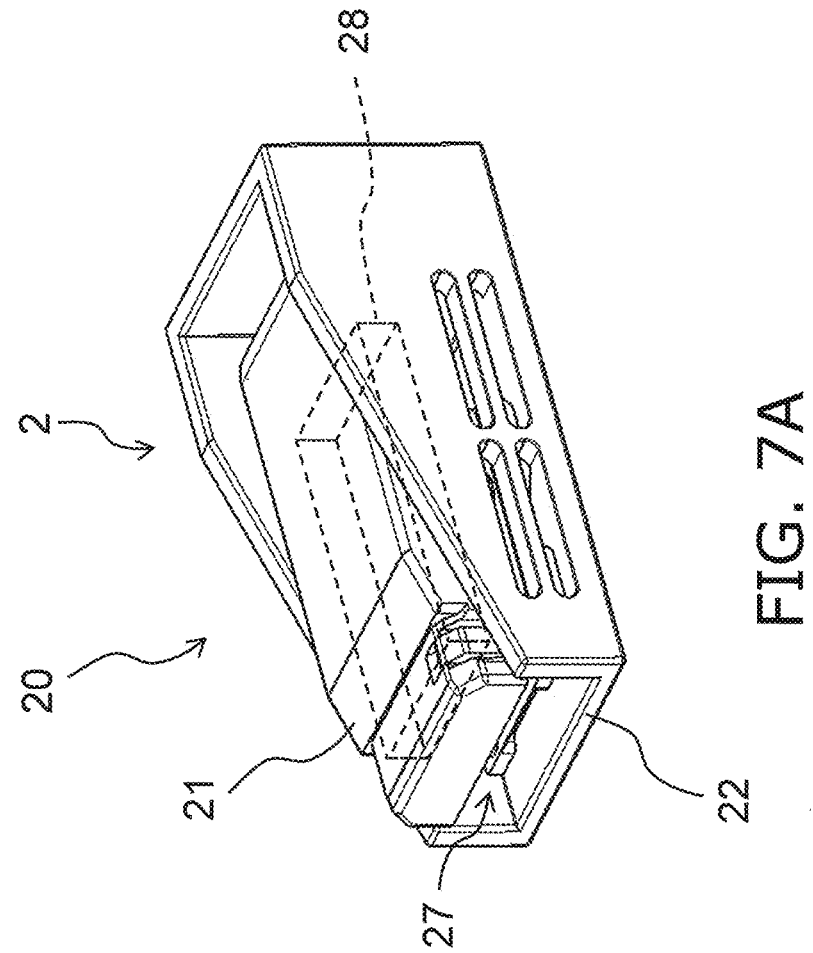
FIG. 7A is a diagram of the configuration of the analysis unit in FIG. 6.

The board unit 28 shown in FIG. 7B is enclosed in the top unit 21 of the analysis unit 2 shown in FIG. 7A.

Figure 8:
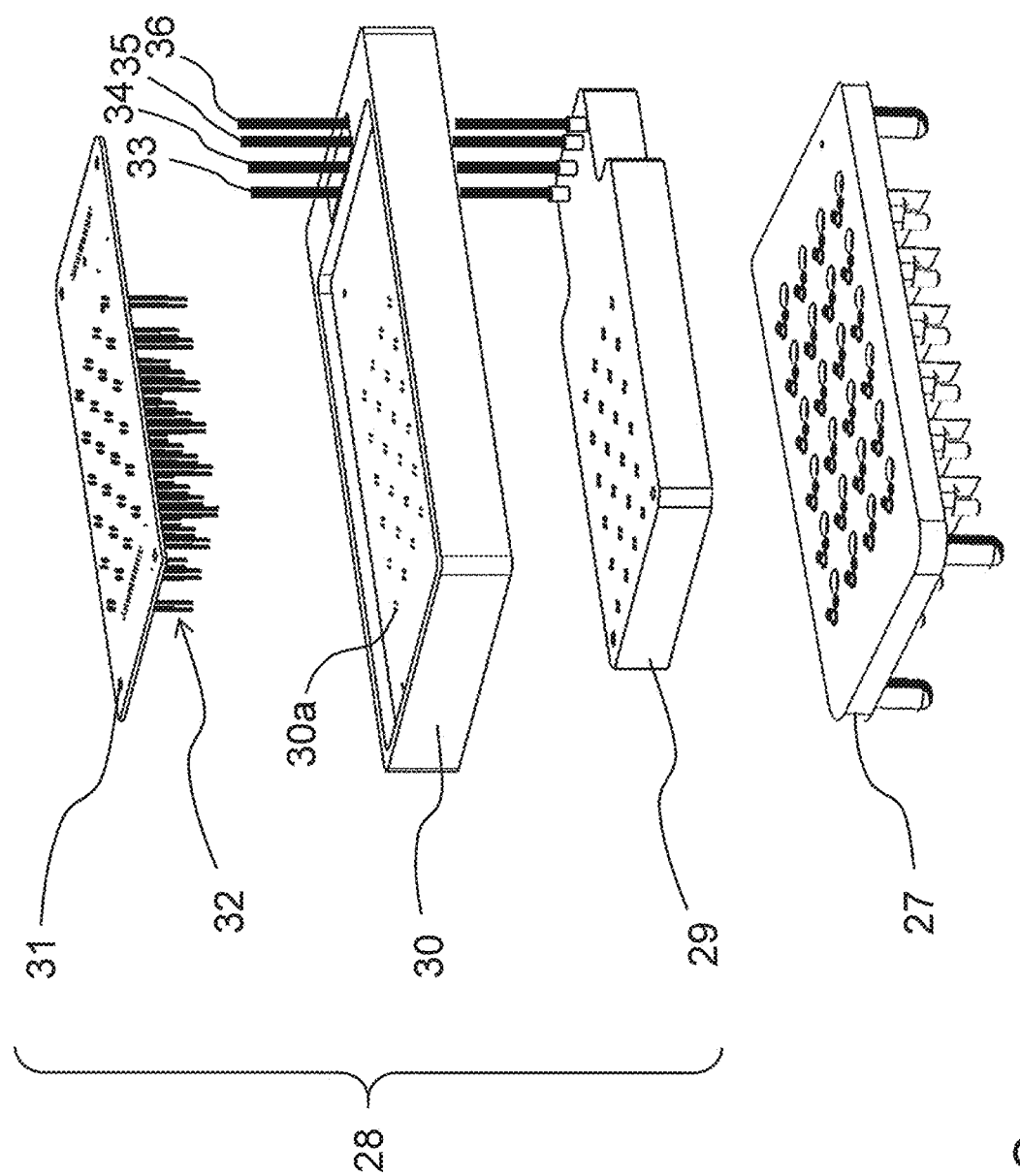
FIG. 8 is an exploded oblique view of the configuration of the board unit included in the analysis unit disposed on the sensor unit.

FIG. 8 shows an exploded oblique view of the board unit 28 disposed on the sensor unit 27. As shown in FIG. 8, the board unit 28 consists of a piping board portion 29, a board base 30, and a board 31, in that order starting from the bottom facing the sensor unit 27.

An air pipe to which an air flow path from the drive unit 3 is connected is enclosed in the piping board portion 29. The board base 30 is provided such that the board 31 is attached to its upper surface. The board 31 is provided with a connecting portion 32 for electrically connecting to an electrochemical sensor 43 (see FIG. 14, etc.) provided to the sensor unit 27 below.

The connecting portion 32 is, for example, a pin-shaped contact probe that conducts merely by contact with a measurement site, such as an electrode, for electrical inspection and testing, and is constituted by a plunger (movable part), a barrel (main body), and an elastic body such as a spring. A plurality of connecting portions 32 are disposed downward from the board 31, pass through the contact through-holes 30a disposed in the board base 30, penetrate the piping board portion 29, and are electrically connected to a plurality of sensors 43 disposed at corresponding positions in the sensor unit 27 below.

A wiring pattern that is electrically connected to the connecting portion 32 is provided on the board 31. The board 31 is connected to an external control unit 4 (see FIG. 1, etc.) via the electrical cable 5.

Figure 9:
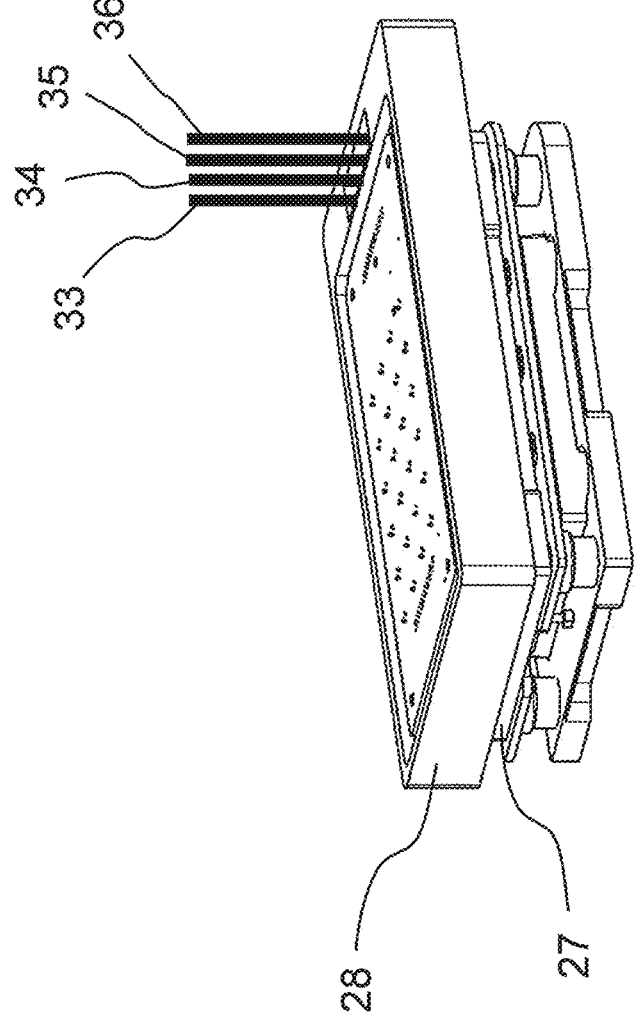
FIG. 9 is an oblique view showing the connected state between the board unit and a piping tube.

FIG. 9 shows the connection state between the board unit 28 and the piping tubes 33, 34, 35, and 36.

In this embodiment, a total of four types of piping tube connected to the drive unit 3 are connected to the board unit 28.

More specifically, the board unit 28 is provided with the piping tube 33 for the additive addition unit A, and the piping tube 34 for the additive addition unit B, as piping tubes for the air supply system to the board unit 28.

Furthermore, the board unit 28 is provided with the intake piping tube 36, as a valve of the intake system for the analysis unit 2.

The piping tube 35 for the stirring member is provided to the board unit 28 as a two-way valve for air supply and intake.

Figure 10:
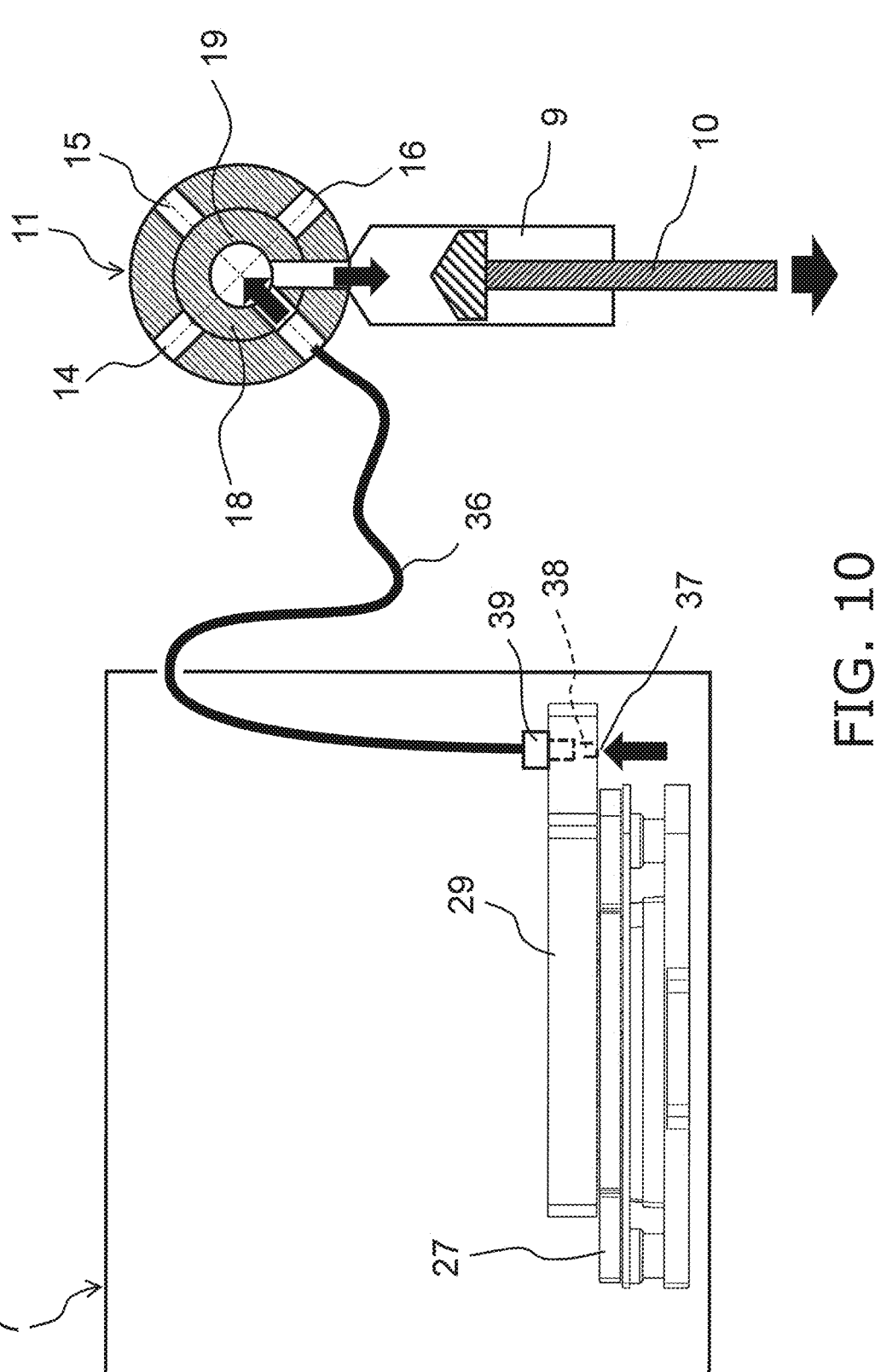
FIG. 10 is a diagram of the configuration of an intake port used as an air pressure supply unit.

FIG. 10 shows the configuration of an intake port used as an air pressure supply.

The air pressure supply unit has an air intake port 37 for drawing in the air in the culture incubator 7 that houses the wells (culture vessels) 25.

More specifically, the air intake port 37 is provided on the lower bottom surface of the piping board portion 29. The air intake port 37 passes through a through-hole 38 in the piping board portion 29 and is connected to the multi-way switching valve 11 of the drive unit 3 via the piping tube 36 connected to the piping tube connecting portion 39 above.

Consequently, the air pressure supply unit has an air intake port 37 for drawing air from the culture incubator 7 that houses the wells 25a, and therefore prevents contamination of the cell culture in the wells 25a.

That is, in this embodiment, the air in the culture incubator 7 that houses the wells 25a, that is, controlled air, is utilized as the air pressure to the additive containers and the stirring members. This prevents contamination of the cell culture in the wells 25a.

Also, since the air intake port 37 is provided on the bottom surface under the piping board portion 29, the inflow of water droplets or the like through the opening of the air intake port 37 can be prevented.

Also, the piping tube 36 is formed using a moisture-permeable material such as a Nafion tube. Consequently, any moisture in the culture incubator 7 can be prevented from flowing into the drive unit 3 described above, and the condensation of dew in the drive unit 3 can also be prevented.

Figures 11A, 11B, 11C:
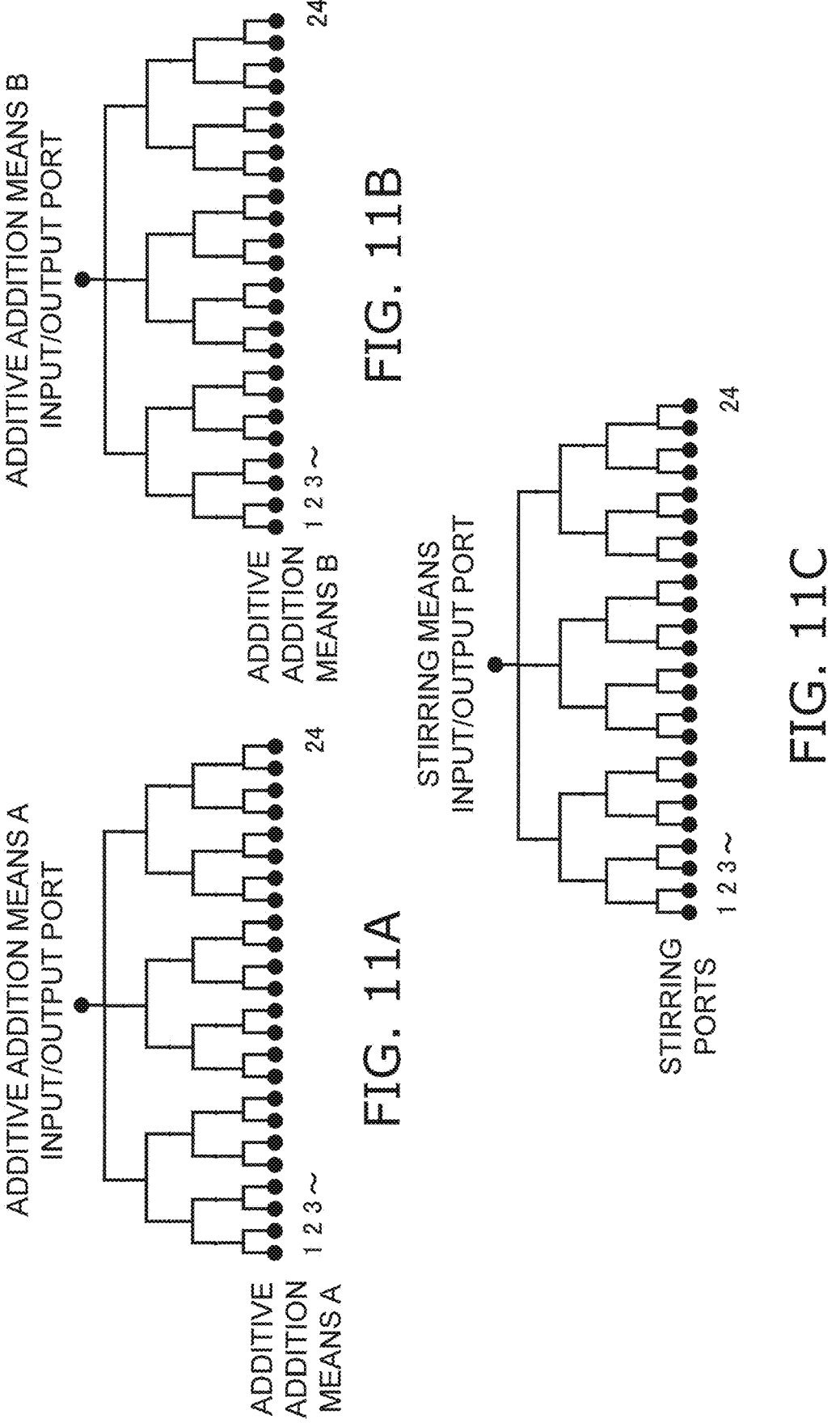
FIGS. 11A to 11C are diagrams of the routes of pipes formed in a piping board portion.

FIGS. 11A to 11C show the routing of the pipes formed in the piping board portion 29.

The piping tube 33 for the additive adding unit A is connected to the piping board unit 29.

Figure 12:
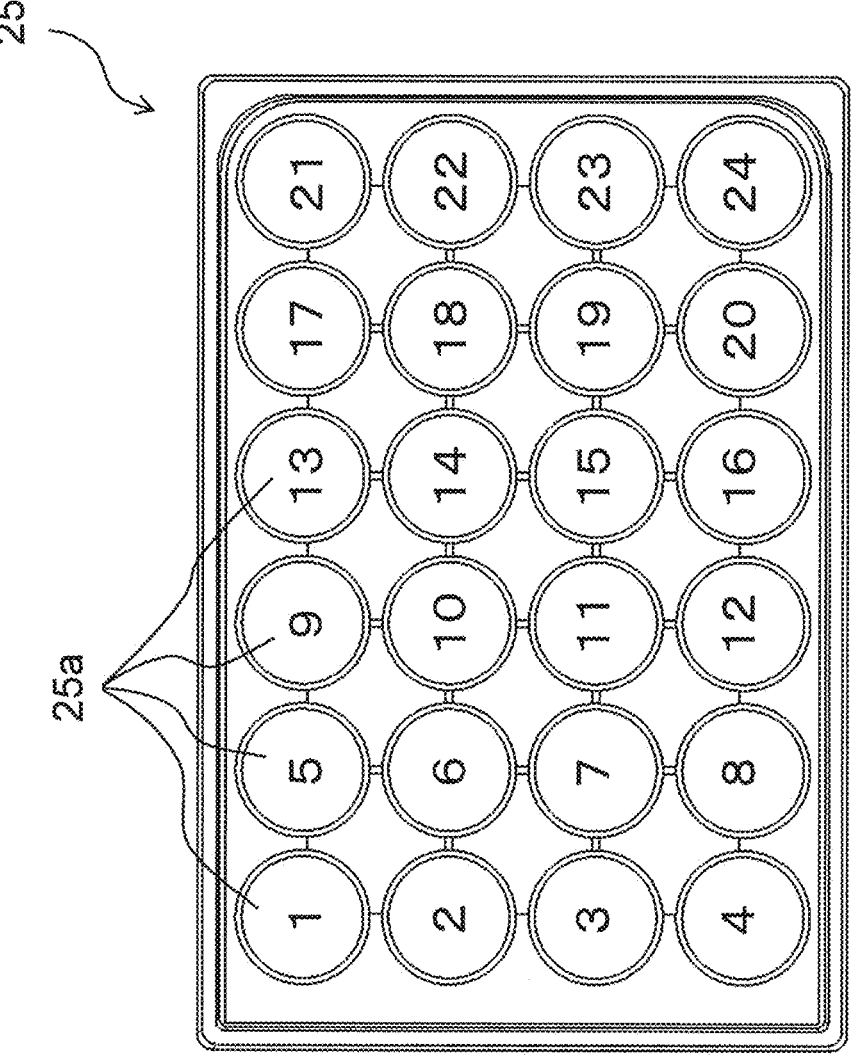
FIG. 12 is a top view of a well plate.

In this embodiment, the well plate 25 used as the culture vessel includes 24 wells 25a, as shown in FIG. 12. Therefore, the pipe for the additive addition unit A branches into 24 parallel pipes, and the outlet openings of the pipes are disposed above specific wells 25a.

Similarly, the piping tube 34 for the additive addition unit B is connected to the piping board portion 29. The pipe for the additive adding unit B is branched into 24 parallel pipes, and the outlet openings of the pipes are disposed above specific wells 25a.

Similarly, the piping tube 35 for the stirring member is connected to the piping board portion 29. The pipe for the stirring member is branched into 24 parallel pipes, and the outlet openings of the pipes are disposed above specific wells 25a.

That is, the same air pressure is simultaneously applied to the additive application portion A of all 24 of the wells 25a. Similarly, the same air pressure is simultaneously applied to the additive application portion B of all 24 of the wells 25a. Similarly, the same air pressure is simultaneously applied to the stirring member of all 24 of the wells 25a.

Figure 13:
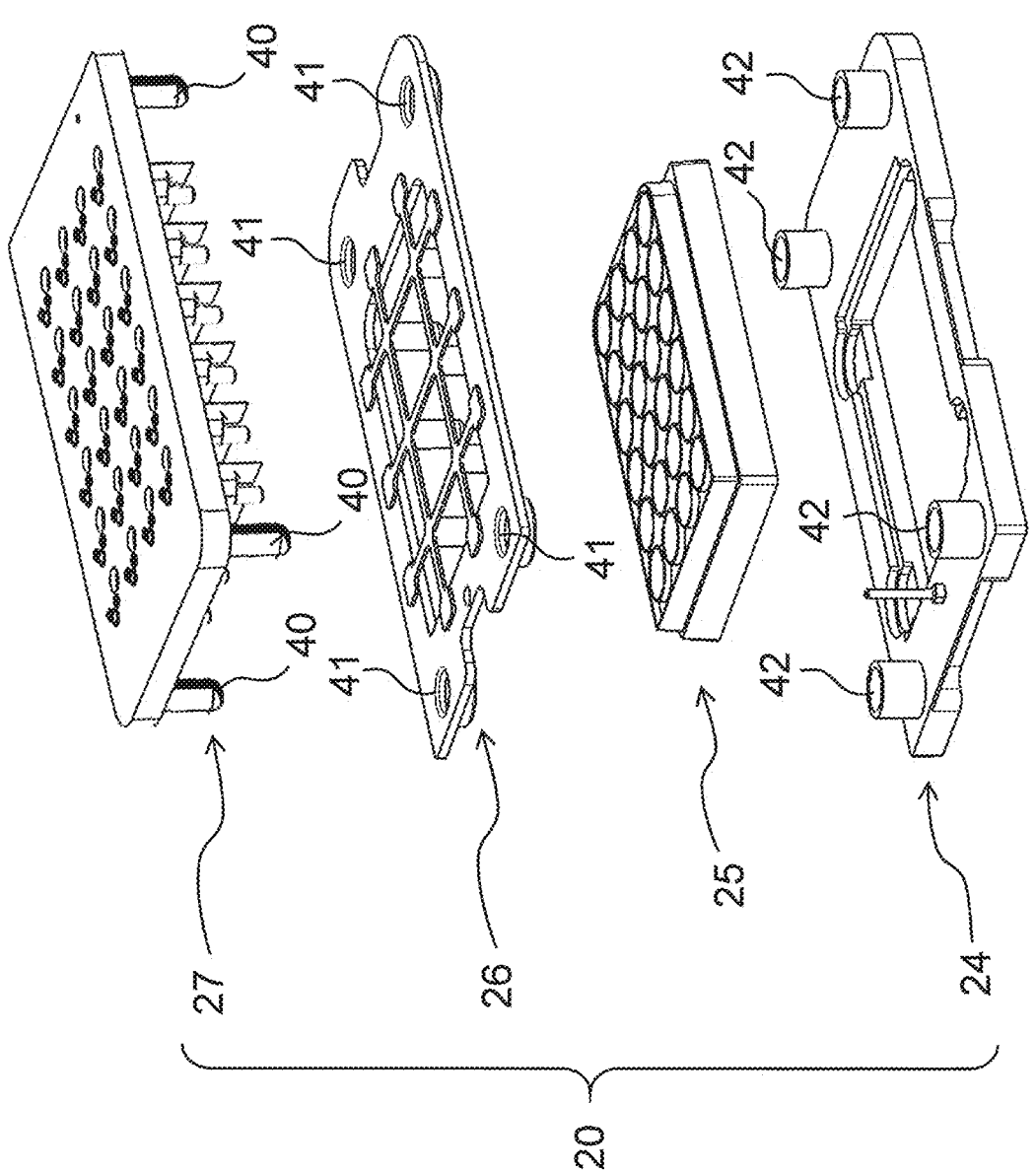
FIG. 13 is an exploded oblique view of the configuration of the adapter unit.

FIG. 13 shows the configuration of the adapter unit 20.

As shown in FIG. 13, the adapter unit 20 has the adapter bottom (culture vessel installation portion) 24, the well plate (culture vessel) 25, the adapter top 26, and the sensor unit 27, disposed in that order starting from the lowest level.

In this embodiment, the well plate 25 has 4×6=24 wells 25a, as shown in FIG. 12.

The adapter top 26 is provided to adjust the height of the well plate 25, and different adapter tops 26 are used according to the height of the well plate 25. This is for adjusting the height relation between the sensor unit 27 and the well plate 25 when the sensor unit 27 is placed on the adapter top 26.

The well plate 25 comes in several types, including a general-purpose type, and the appropriate adapter top 26 is used to match the type.

The sensor unit 27 disposed on the adapter top 26 has four legs (support bodies) 40 provided on its lower surface, which pass through through-holes 41 in the adapter top 26 below and are inserted into positioning holes 42 provided in the adapter bottom 24 serving as a culture vessel installation portion.

Consequently, the sensor unit 27 is installed above the well plate 25 with a specific spacing in between. In other words, the sensor unit 27 is provided with the legs 40 to ensure enough space above the adapter bottom 24 to house the well plate 25. The sensor unit 27 is disposed on the adapter bottom 24 in a state of being supported by the legs 40.

As discussed above, the legs 40 support the sensor unit 27 with respect to the adapter bottom 24 in order to ensure enough space above the adapter bottom 24 to house the well plate 25 (the gap between the upper surface of the adapter bottom 24 and the lower surface of the sensor unit 27).

Here, the support bodies for supporting the sensor unit 27 are not limited to the legs 40 provided to the sensor unit 27. For example, the support bodies may be provided on the adapter bottom 24 side, so long the sensor unit 27 is supported from below with respect to the adapter bottom 24.

Figure 14:
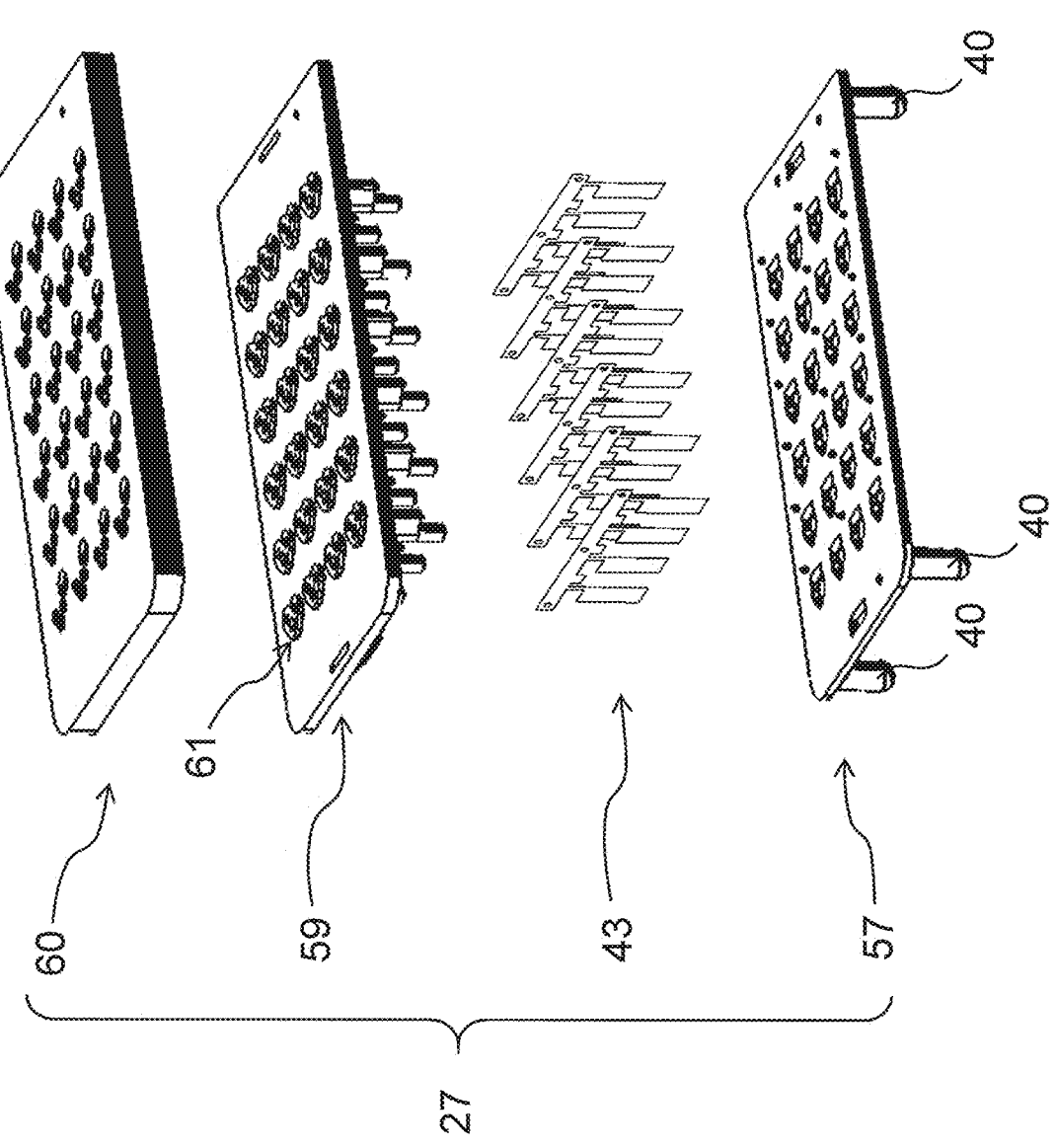
FIG. 14 is an exploded oblique view of the configuration of the sensor unit.

FIG. 14 shows the configuration of the sensor unit 27.

As shown in FIG. 14, the sensor unit 27 includes a bottom plate 57, the plurality of sensors 43, a top plate 59 having a port 61 for supplying an additive, and a gasket sheet 60, in that order starting from the bottom.

Figure 15:
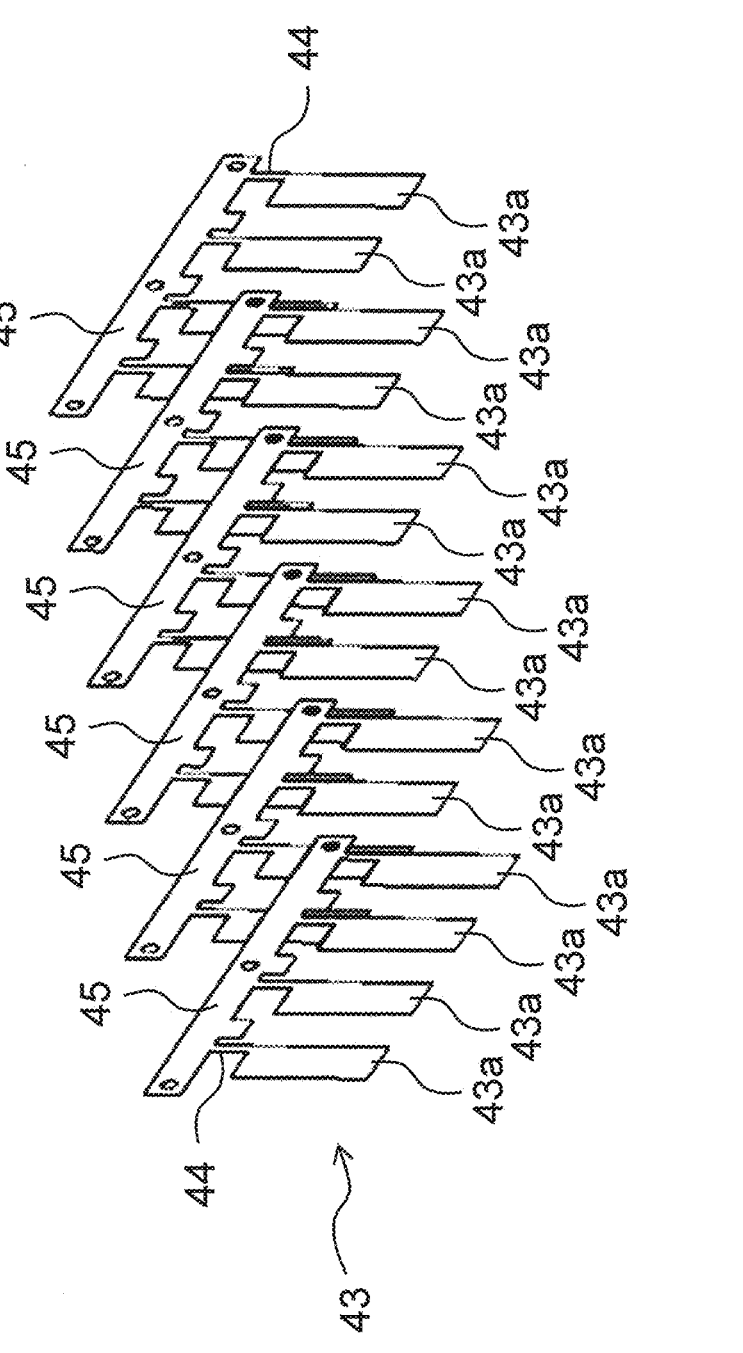
FIG. 15 is an oblique view of the configuration of the sensors included in the sensor unit in FIG. 14.

In this embodiment, as shown in FIG. 15, the plurality of sensors 43 included in the sensor unit 27 are such that the upper end portions of the main bodies 43a of the four sensors 43 are linked by linking portions 45 via the bending portions 44.

As shown in FIG. 14, six sets of the sensors 43, each having four sensors 43, are attached to the bottom plate 57.

Figure 16:
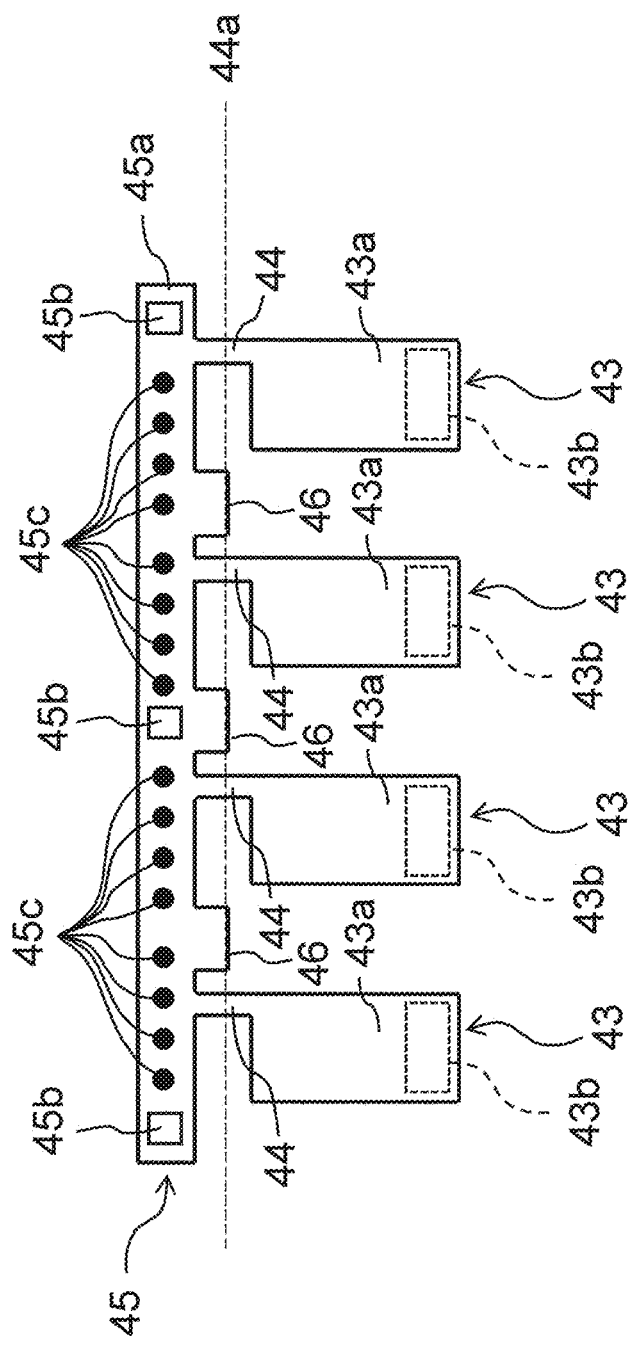
FIG. 16 is a plan view of the configuration of the sensors in FIG. 15.

The sensor 43 is configured, for example, by forming a gold electrode layer by sputtering on the upper surface of a PET (polyethylene terephthalate) film, which is a resin material. As shown in FIG. 16, the sensors 43 each have a main body 43a, a sensing unit 43b, a bending portion 44, a linking portion 45, and a contact portion 46.

The main body 43a is a substantially rectangular flat member, and is linked at its upper end portion to the bending portion 44.

The sensing unit 43b is provided on the surface of the lower part of the substantially rectangular main body 43a, and includes measurement electrodes (working electrode, counter electrode, and reference electrode). When a specific voltage is applied to each measurement electrode of the sensing unit 43b immersed in the culture medium contained in the well 25a, the concentration of a specific component of the culture medium is measured electrochemically.

Each measurement electrode included in the sensing unit 43b is formed by evaporating and dividing an electrode layer with a laser.

Here, when the concentration of glucose in the culture medium is to be measured, the reagent layer immobilized on the surface of the working electrode can contain a glucose oxidase, such as glucose oxidase (GOx) or glucose dehydrogenase (GDH), or a redox mediator.

The glucose that permeates in from the culture medium through the protective film is oxidized into gluconolactone by a reaction with an enzyme (such as GOx or GDH) in the reagent layer, and the glucose concentration is measured by converting the reductant of the redox mediator produced at the same time, or the electrons generated by the oxidation reaction of hydrogen peroxide, into a current value.

As shown in FIG. 16, the bending portion 44 is a portion that links the main body 43a and the linking portion 45, and is bent at an approximate right angle along the bending line 44a. As a result, the linking portion 45 is disposed substantially perpendicular to the main body 43a.

Also, as shown in FIG. 16, the bending portion 44 has a smaller width (the dimension in the left and right direction in the drawing) than the main body 43a. That is, the bending portion 44 is formed as if cut out to leave a portion thinner than the main body 43a. Consequently, when the linking portion 45 is bent with respect to the main body 43a, less force is required for bending along the bending line 44a, so the linking portion 45 can be easily bent.

As shown in FIG. 16, the linking portion 45 links the upper end portions of the main bodies 43a of four sensors 43 to each other via the bending portions 44. The linking portion 45 has a main body 45a, positioning holes (latching mechanisms) 45b, contact portions 45c, and contact portions 46.

The main body 45a is disposed in a direction substantially perpendicular to the lengthwise direction of the main bodies 43a of the substantially I-shaped sensors 43, and links the main bodies 43a of four sensors 43 to each other via the bending portions 44.

The positioning holes 45b are latched in a state in which prongs (latching mechanisms) 57c (see FIG. 24A, etc.) provided to the bottom plate 57 side are inserted during the step of assembling the sensor unit 27 (discussed below). This positions the sensors 43 with respect to the bottom plate 57.

The contact portions 45c are disposed in groups of four, each group corresponding to the sensing unit 43b of one sensor 43, and are electrically connected to the measurement electrodes (working electrode, counter electrode, and reference electrode) included in the sensing units 43b disposed at the lower parts of the main bodies 45a of the sensors 43.

As shown in FIG. 16, the contact portions 46 are portions formed to protrude downward from the lower part of the linking portion 45, and the lower end surfaces thereof are disposed along the straight line of the bending line 44a. The contact portions 46 come into contact with the upper surface of the bottom plate 57 in the step of assembling the sensor unit 27 (discussed below), which positions the sensors 43 with respect to the bottom plate 57.

As shown in FIG. 15, the sensor unit 27 in this embodiment is configured to include the plurality of sensors 43 for measuring a component of the culture medium in the culture vessels, and comprises the sensors 43 each having the main body 43a and a sensing unit 43b that is disposed at the lower end side of the main body 43a and is immersed in a culture medium to measure a component of the culture medium, and the linking portion 45 that links the plurality of sensors 43 on the upper end side of the main body 43a.

Consequently, the plurality of sensors 43 are attached to the bottom plate 57 in a state of being linked together by the linking portion 45, so the positions of the linked sensors 43 can be accurately defined.

Consequently, the positional accuracy (position, angle, etc.) of each sensor 43 with respect to the plurality of wells (culture vessels) 25a included in the well plate 25 can be increased.

As a result, the immersion depth of each sensor 43 in the culture medium contained in a well 25a is substantially consistent, so stable measurement results can be obtained.

Sensor Unit 27 Assembly Step

Here, the step of assembling the sensor unit 27, including the step of attaching the sensors 43 to the bottom plate 57, will now be described with reference to FIGS. 17 to 27.

Figure 17:
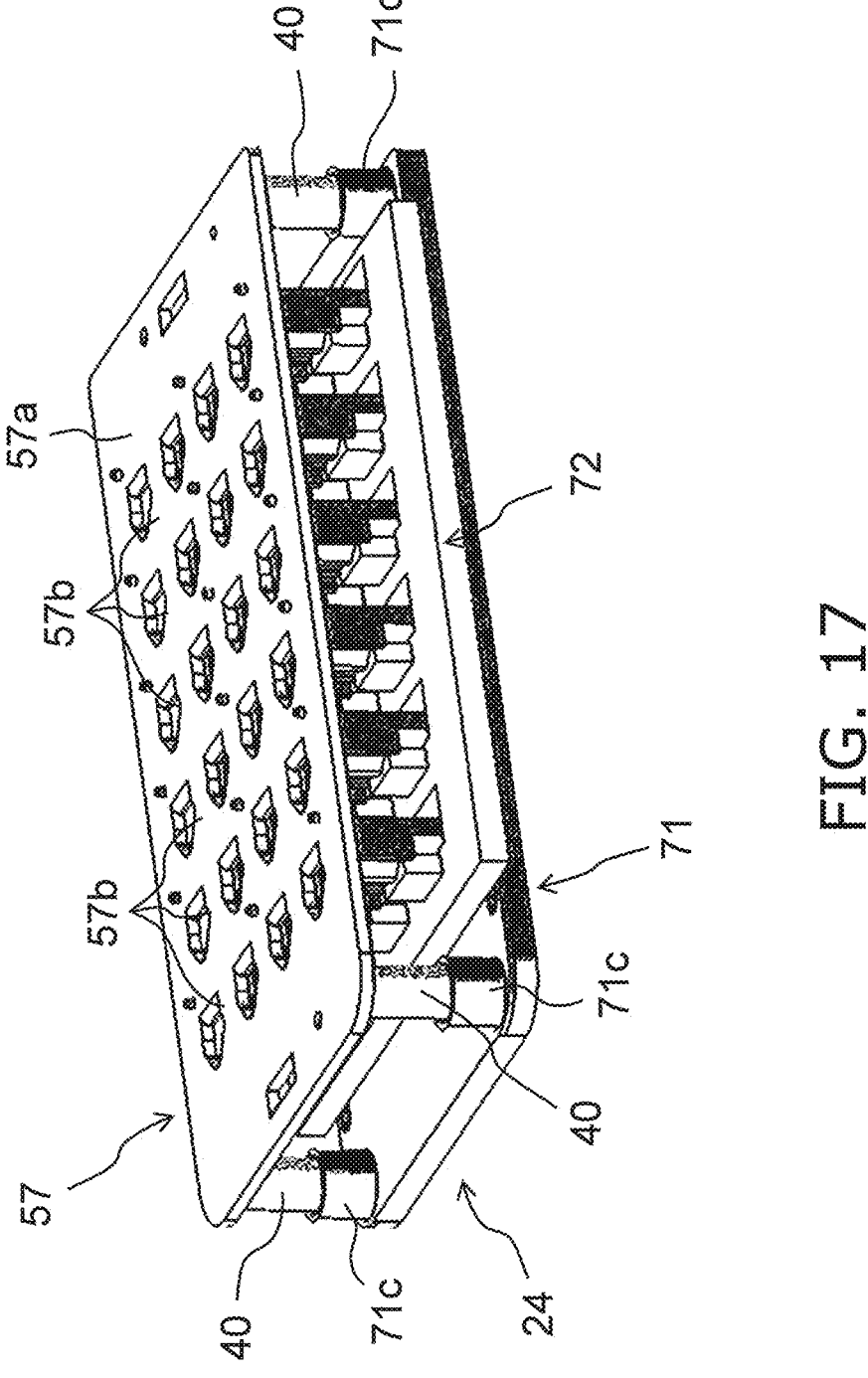
FIG. 17 is an oblique view showing a state in which a sensor fixing jig is put in place in the assembly of the sensor unit of FIG. 14.

In the step of assembling the sensor unit 27, first, a set of four sensors 43 whose upper ends are linked by the linking portion 45 is attached to the bottom plate 57 using sensor fixing jigs 71 and 72 as shown in FIG. 17.

The sensor fixing jigs 71 and 72 are used for accurately positioning the sensing units 43b of the sensors 43 with respect to the wells 25a included in the well plate 25 so that the sensing units 43b will be at a specific immersion depth.

As shown in FIG. 17, the sensor fixing jigs 71 and 72 are used in a state in which the bottom plate 57 is disposed on the upper surface side of the jigs.

At this point, the legs 40 of the bottom plate 57 are inserted as shown in FIG. 17 into the positioning portions 71c of the sensor fixing jig 71. The sensor fixing jig 72 is attached to the upper surface of the sensor fixing jig 71 in a state of being able to slide relative to the sensor fixing jig 71.

Consequently, the sensor fixing jigs 71 and 72 are accurately positioned with respect to the bottom plate 57.

Figures 18A, 18B, 18C:
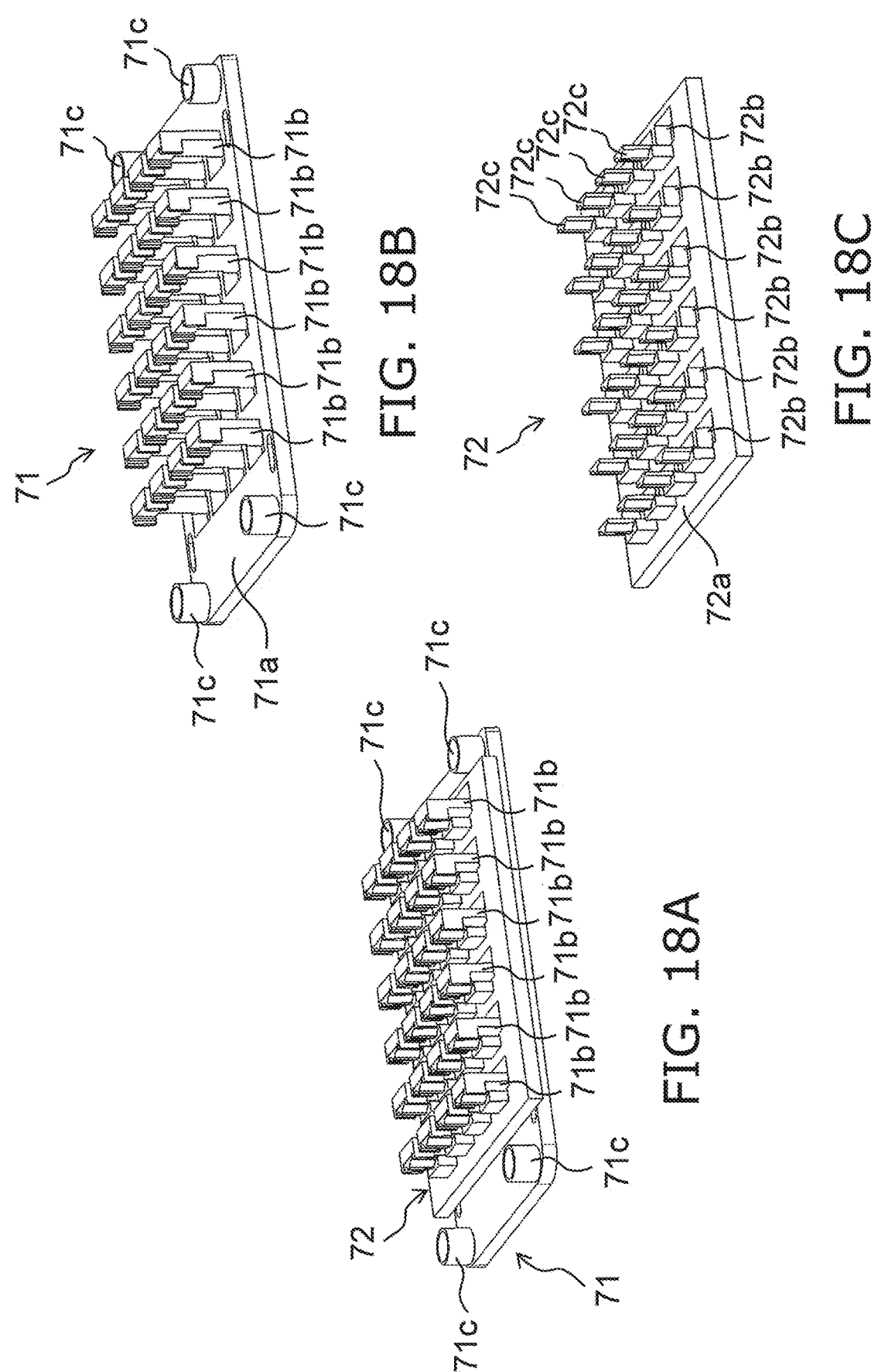
FIGS. 18A to 18C are oblique views of the configuration of the sensor fixing jig in FIG. 15.

As shown in FIG. 18A, the sensor fixing jigs 71 and 72 are used in a state in which the sensor fixing jig 72 is disposed overlapping the upper surface of the sensor fixing jig 71.

As shown in FIG. 18B, the sensor fixing jig 71 has a base portion 71a, holding portions 71b, and positioning portions 71c.

The base portion 71a is a plate-like member, and has a plurality of holding portions 71b and positioning portions 71c provided on its upper surface.

The holding portions 71b are portions that hold the main bodies 43a of the sensors 43 along with the contact portions 72c on the sensor fixing jig 72 side when the sensors 43 are attached (discussed below), and are provided protruding upward from the upper surface of the base portion 71a. Also, in this embodiment, the holding portions 71b are provided in a number corresponding to the number of sensors 43 (24).

The positioning portions 71c are disposed at the four corners of the upper surface of the base portion 71a, and the legs 40 of the bottom plate 57 are inserted therein. This positions the bottom plate 57 with respect to the sensor fixing jig 71.

The sensor fixing jig 72 is used in a state of being disposed on the upper surface of the sensor fixing jig 71, and has a base portion 72a, through-holes 72b, and contact portions 72c, as shown in FIG. 18C.

The base portion 72a is a plate-like member, and is provided with the through-holes 72b and the contact portions 72c.

The through-holes 72b are holes that communicate between the upper surface and the lower surface of the plate-like base portion 72a, and the above-mentioned holding portions 71b on the sensor fixing jig 71 side are inserted into the corresponding through-holes 72b.

The contact portions 72c are portions that hold the main bodies 43a of the sensors 43 along with the holding portions 71b on the sensor fixing jig 71 side when the sensor 43 (discussed below) is attached, and are provided so as to protrude upward from positions adjacent to the through-holes 72b on the upper surface of the base portion 72a. Also, in this embodiment, the contact portions 72c are provided in a number corresponding to the number of sensors 43 (24).

Figure 19:
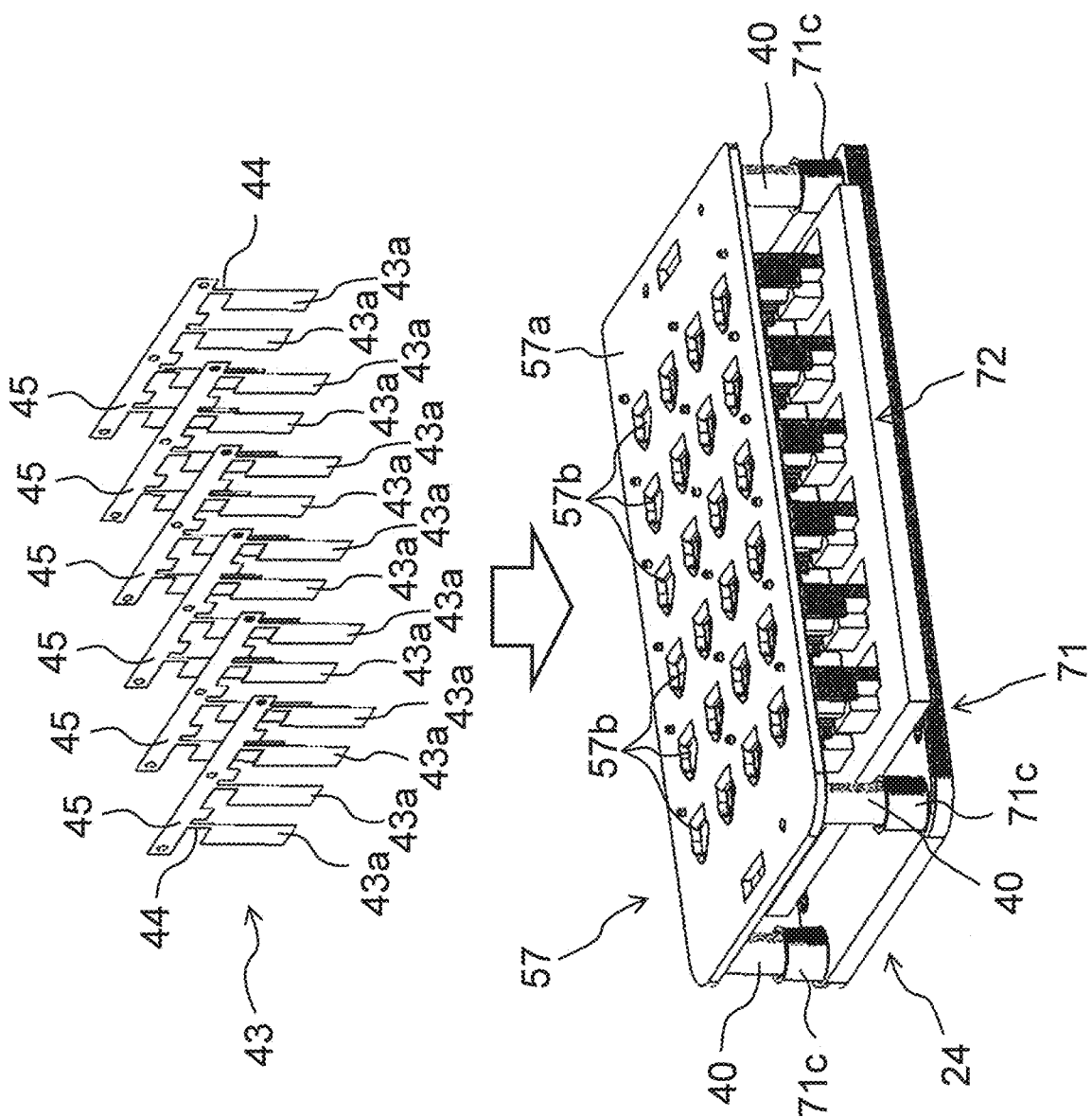
FIG. 19 is an oblique view showing a state in which the sensors are inserted into through-holes in the bottom plate in the assembly of the sensor unit in FIG. 14.

Next, as shown in FIG. 19, six sets (4×6=24) of sensors 43 are inserted into through-holes 57b formed in the plate 57 in a state in which the bottom plate 57 is disposed on the upper surface side of the sensor fixing jigs 71 and 72.

Figure 20:
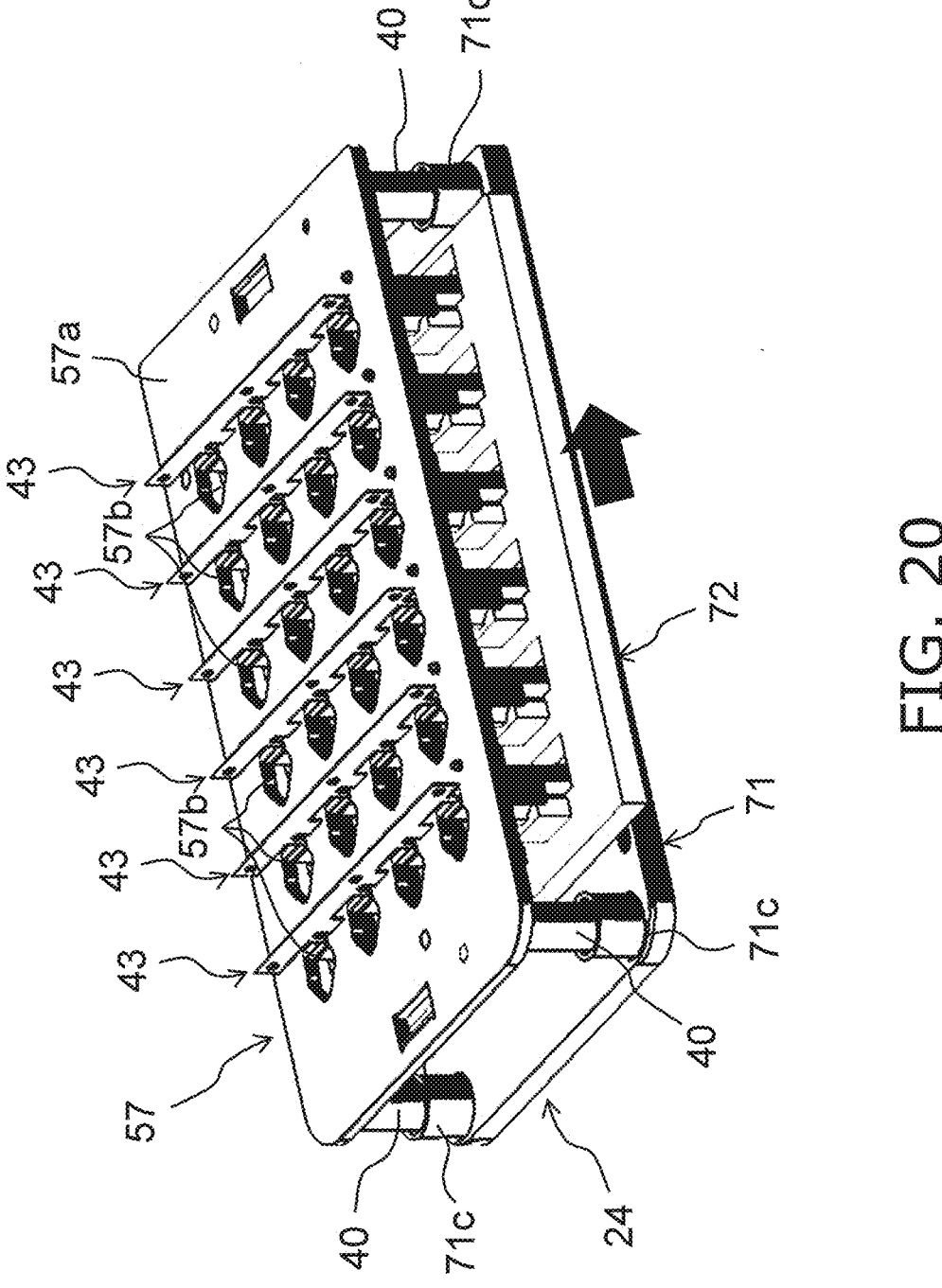
FIG. 20 is an oblique view showing a state in which the sensor fixing jig is slid to hold the main bodies of the sensors in the assembly of the sensor unit in FIG. 14.

When the sensors 43 are inserted into the through-hole 57b of the bottom plate 57, the contact portions 46 of the sensors 43 come into contact with the upper surface of the bottom plate 57 as shown in FIG. 20.

At this point, as discussed above, the contact portions 46 are disposed along the straight line of the bending line 44a, so the bending portions 44 can be bent along the bending line 44a, with the contact portions 46 as the starting point, in a state in which the contact portions 46 are in contact with the upper surface of the bottom plate 57.

Consequently, the sensors 43 bent along the bending line 44a with the contact portions 46 as the starting point will be accurately disposed facing downward from the through-holes 57b in the bottom plate 57, so the positional accuracy of the sensors 43 with respect to the wells 25a can be increased.

Also, as shown in FIG. 20, the sensor fixing jig 72 slides in the direction of the arrow (to the right) with respect to the sensor fixing jig 71 in a state in which the sensors 43 are inserted into the through-holes 57b in the bottom plate 57.

Figures 21A, 21B:
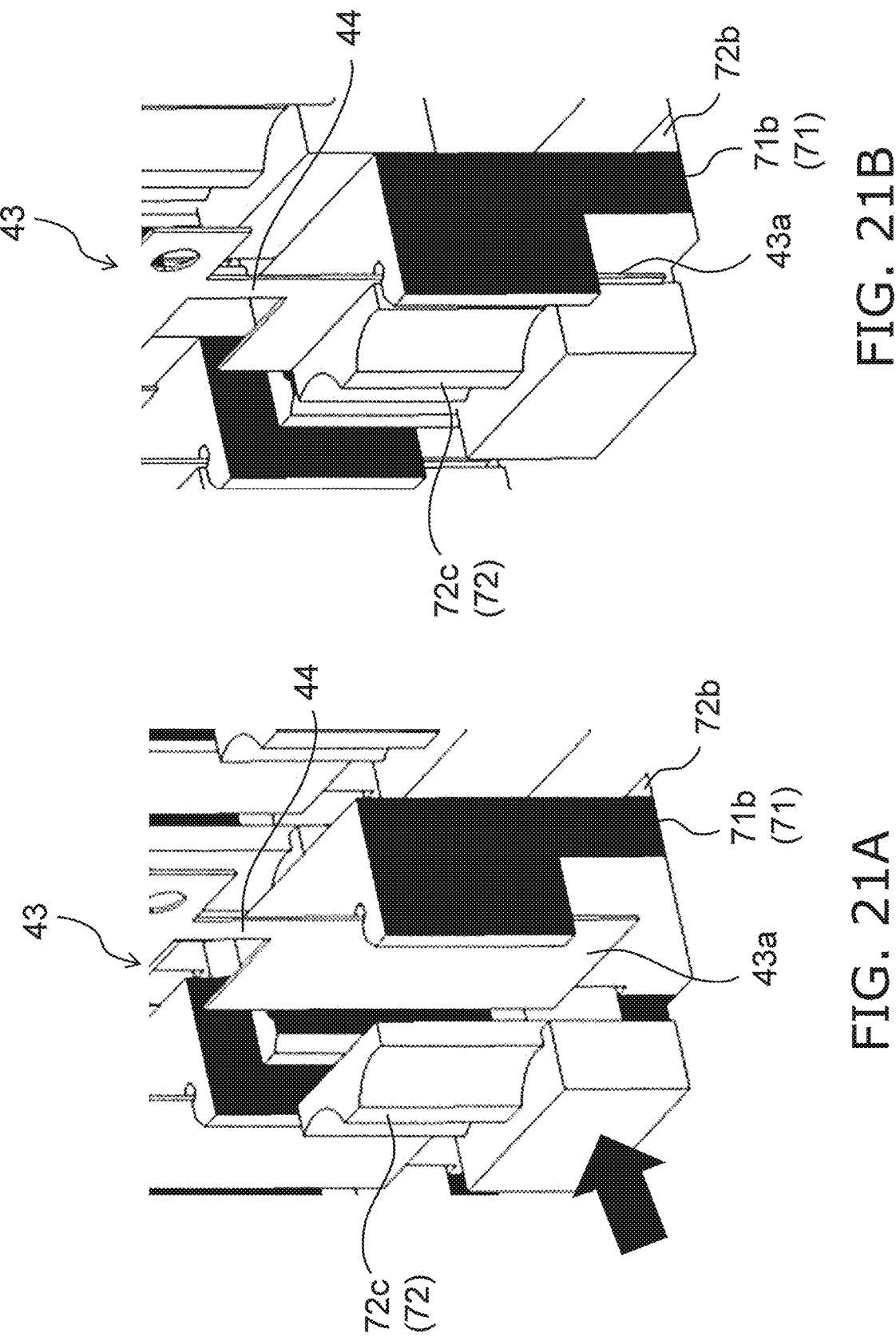
FIGS. 21A and 21B are detail oblique views showing a state in which the main body of a sensor is held by the sensor fixing jig in the assembly of the sensor unit in FIG. 14.

Here, the main bodies 43a of the sensors 43 inserted into the through-holes 57b in the bottom plate 57 pass through the through-holes 72b in the sensor fixing jig 72 and are held on one side by the holding portions 71b of the sensor fixing jig 71 that protrude upward, as shown in FIG. 21A.

From this state, as shown in FIG. 21A, when the sensor fixing jig 72 slides relative to the sensor fixing jig 71 in the direction of the arrow in the drawing, the main bodies 43a of the sensors 43 are held in a state in which both sides are sandwiched between the holding portions 71b of the sensor fixing jig 71 and the contact portions 72c of the sensor fixing jig 72 as shown in FIG. 21B.

As a result, the main bodies 43a of the sensors 43 are accurately positioned by the sensor fixing jigs 71 and 72.

Figures 22A, 22B:
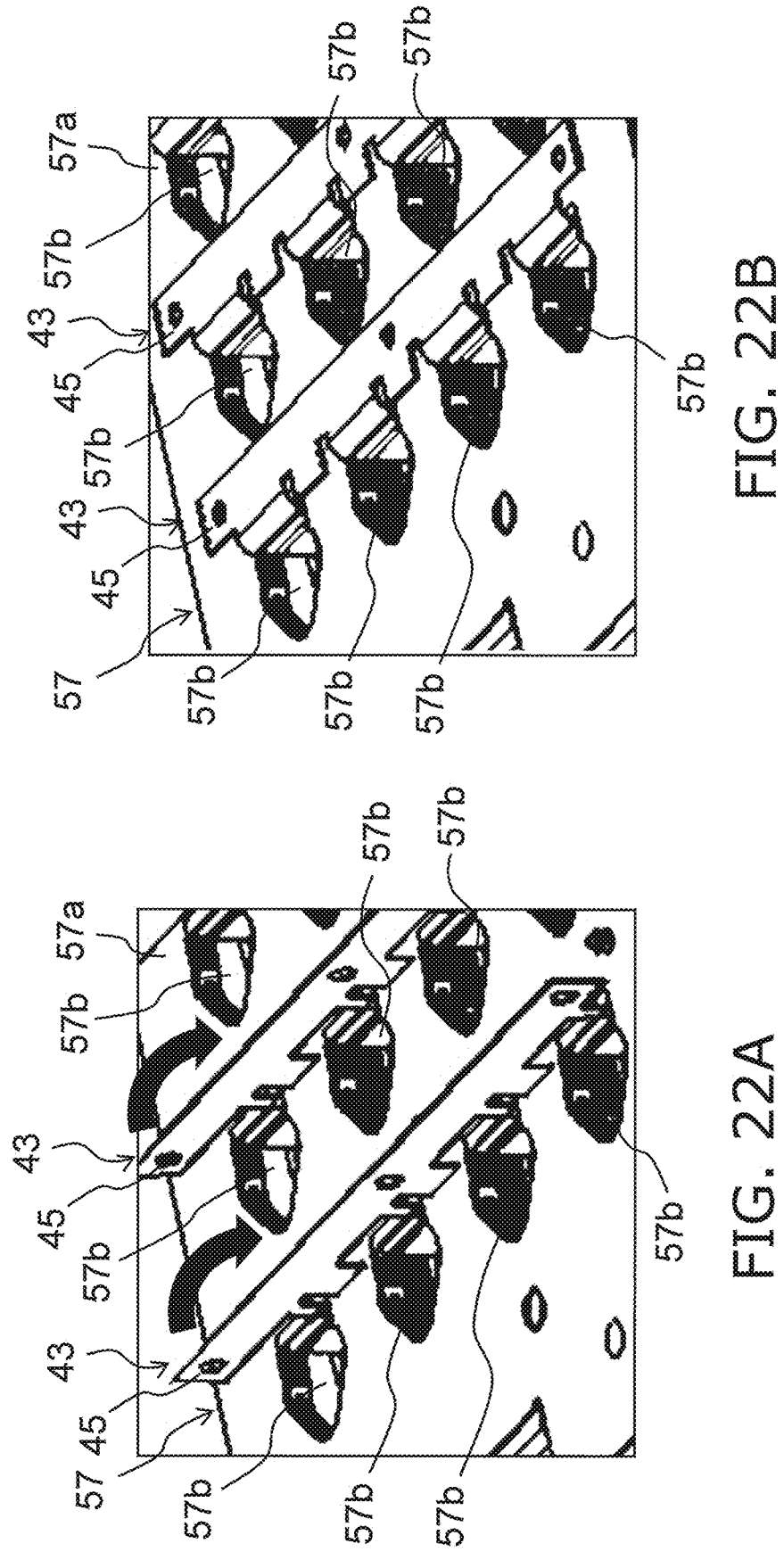
FIGS. 22A and 22B are detail oblique views showing a step of bending the linking portion in the assembly of the sensor unit in FIG. 14.

Next, while the main bodies 43a of the sensors 43 are still held by the sensor fixing jigs 71 and 72, the linking portion 45 is bent so as to be substantially parallel to the upper surface of the bottom plate 57, as shown in FIG. 22A (see the arrow in the drawing).

The bending of the linking portion 45 may be performed manually, or with a tool such as a bending jig, or may be automatically performed by a robot hand or the like.

At this point, as discussed above, the main bodies 43a of the sensors 43 are held by the sensor fixing jigs 71 and 72 in a state of having been inserted into the through-holes 57b of the bottom plate 57. Therefore, when the bending portions 44 are bent along the bending line 44a with the contact portions 46 as the starting point, the linking portion 45 is bent substantially parallel to the upper surface of the bottom plate 57 as shown in FIG. 22B.

Figures 23A, 23B:
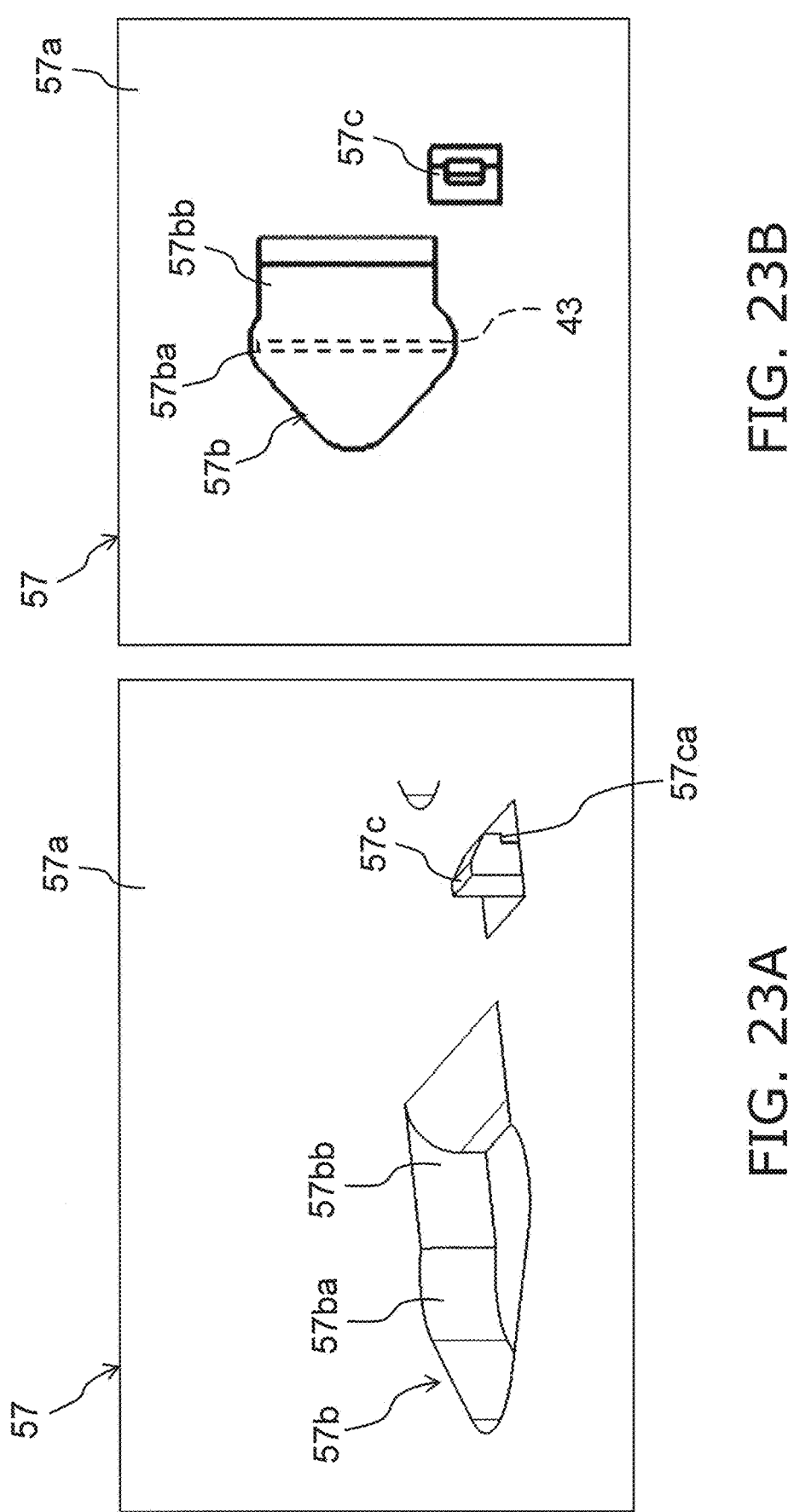
FIGS. 23A and 23B are detail oblique and plan views of a through-hole and a prong formed in the bottom plate in FIG. 19.

Furthermore, in the state shown in FIG. 22B, three through-holes 57b and three prongs 57c are disposed for one set of four sensors 43 on the upper surface of the plate portion 57a of the bottom plate 57, as shown in FIGS. 23A and 23B.

As shown in FIG. 23B, the through-holes 57b are formed so as to include a wide insertion portion 57ba and a holding portion 57bb that is narrower than the insertion portion 57ba when viewed from above.

Consequently, when a sensor 43 is inserted into a through-hole 57b, as shown in FIG. 23B, it is first inserted into the wide insertion portion 57ba and then moved to the narrow holding portion 57bb side and held there.

As a result, the sensor 43 is held in a state in which its movement is restricted in the upward direction.

Also, as discussed above, the prong 57c is provided on the upper surface of the plate portion 57a of the bottom plate 57, as shown in FIGS. 23A and 23B.

The prong 57c is formed integrally with the plate portion 57a, is provided so as to protrude upward from the upper surface thereof, and latches the linking portion 45 by being inserted into the positioning hole 45b formed in the linking portion 45.

As a result, the prong 57c and the positioning hole 45b function as a latching mechanism, so that the linking portion 45 can be accurately latched at a specific position on the upper surface of the bottom plate 57.

Therefore, since the linking portion 45 is accurately positioned with respect to the upper surface of the bottom plate 57, the main bodies 43a of the sensors 43 connected via the bending portions 44 can also be accurately positioned.

Figures 24A, 24B:
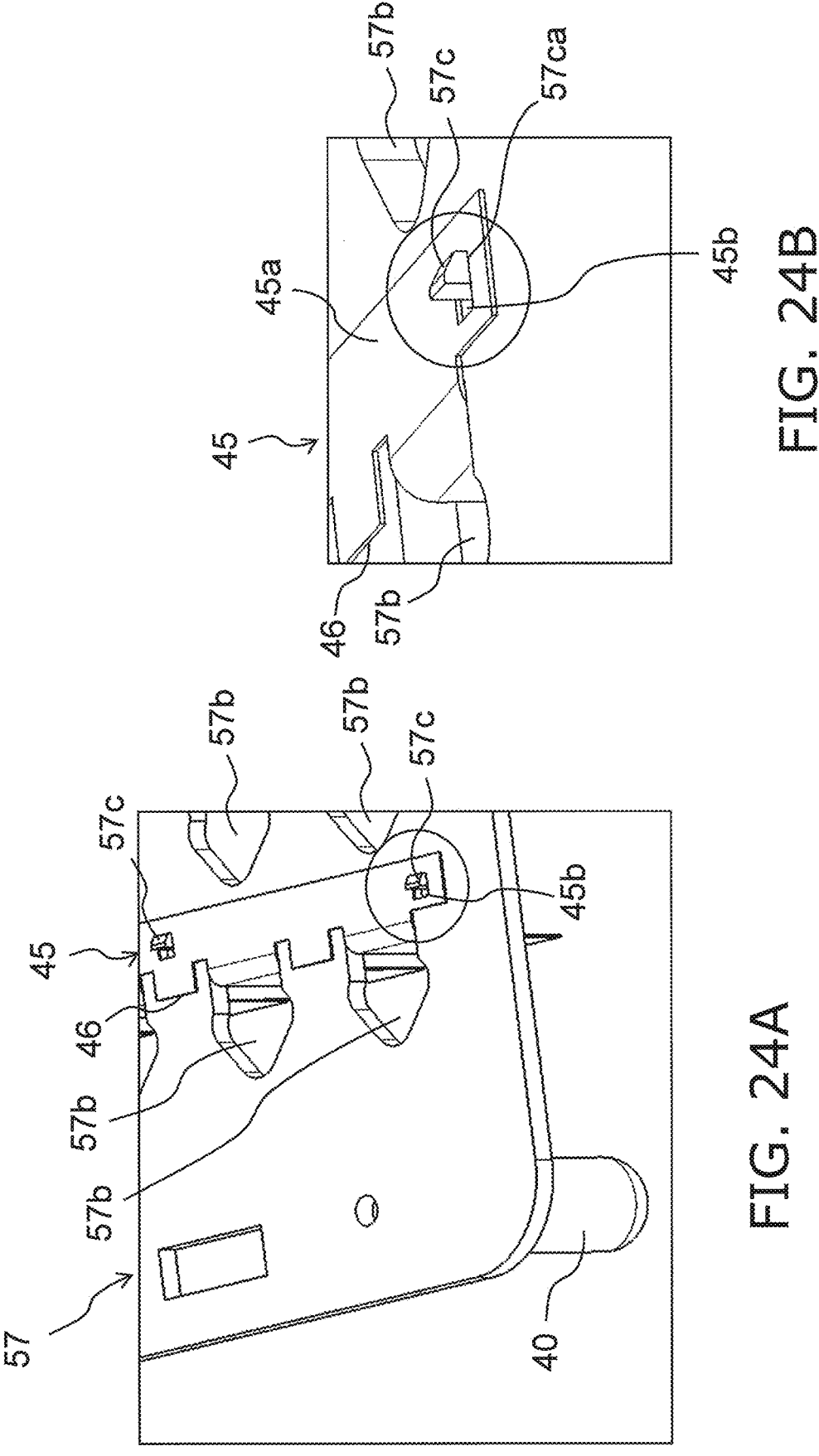
FIG. 24A is an oblique view showing a state in which the linking portion that links the upper end portion of a sensor inserted into a through-hole in the bottom plate in FIG. 23 is latched by a prong.
FIG. 24B is a detail oblique view thereof.

In the state shown in FIGS. 24A and 24B, the holding surface 57ca of the prong 57c holds the upper surface of the linking portion 45 so as to hold this surface down.

Consequently, the linking portion 45 is held substantially parallel to the upper surface of the bottom plate 57.

Figure 25:
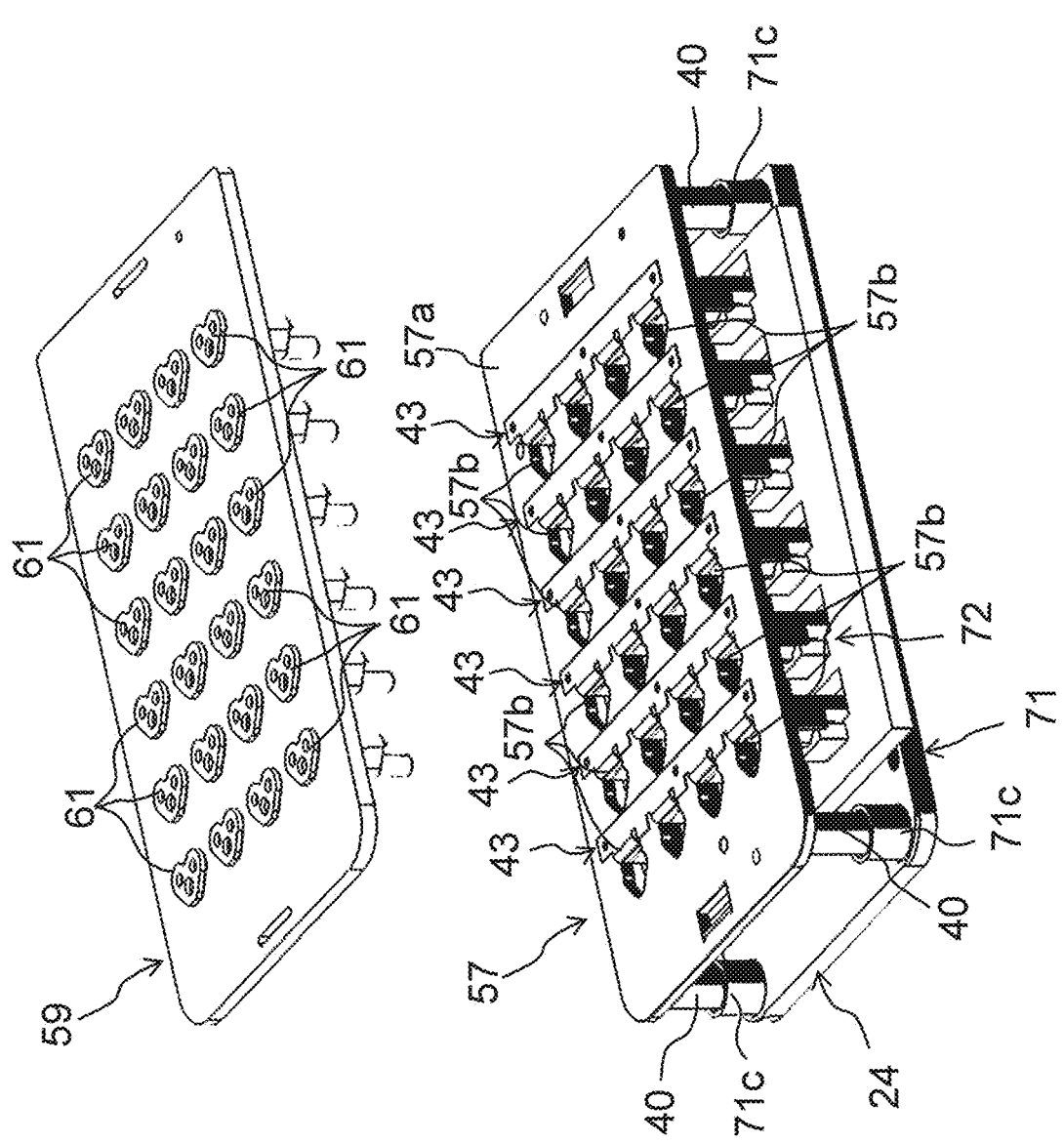
FIG. 25 is an oblique view showing the step of attaching the top plate on the bent linking portion shown in FIG. 22B.

Next, as shown in FIG. 25, the top plate 59 is placed on the upper surface of the bottom plate 57 in a state in which the linking portion 45 has been bent.

Figure 26:
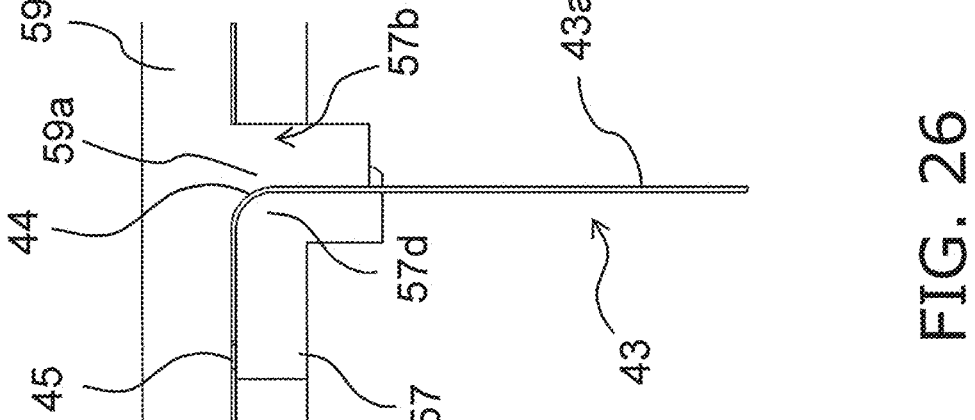
FIG. 26 is a cross-sectional view showing a sensor held between the bottom plate and the top plate.

At this point, each sensor 43 disposed so as to be sandwiched between the lower surface of the top plate 59 and the upper surface of the bottom plate 57 is held between a support portion 57d on the top plate 59 side and a pressing portion 59a on the bottom plate 57 side, as shown in FIG. 26.

That is, the support portion 57d that supports the lower side of the bending portion 44 of the sensor 43 is provided at the opening edge of the through-hole 57b of the bottom plate 57. The pressing portion 59a that presses the upper side of the bending portion 44 of the sensor 43 downward is provided to the portion of the top plate 59 that is opposite the support portion 57d.

Consequently, the upper surface of the sensor 43 is supported by the pressing portion 59a, and the lower surface supported by the support portion 57d provided on the upper surface side of the bottom plate 57.

As shown in FIG. 26, the support portion 57d has an upper surface curved portion shape that includes a curved upper surface. Also, as shown in FIG. 26, the pressing portion 59a has a lower surface curved portion shape that includes a curved lower surface.

As a result, as shown in FIG. 26, when the sensor 43 is sandwiched from above and below by the top plate 59 and the bottom plate 57, the bending portion 44 of the sensor 43 is held in a state of being sandwiched from above and below by the support portion 57d and the pressing portion 59a.

Therefore, since the bending angle of the sensor 43 is accurately defined, the sensing unit 43b provided at the lower end portion of the main body 43a of the sensor 43 is disposed in a stable state.

As a result, the sensing accuracy can be improved by accurately managing the immersion depth of the sensing units 43b immersed in the culture medium in the wells 25a included in the well plate 25.

Figure 27:
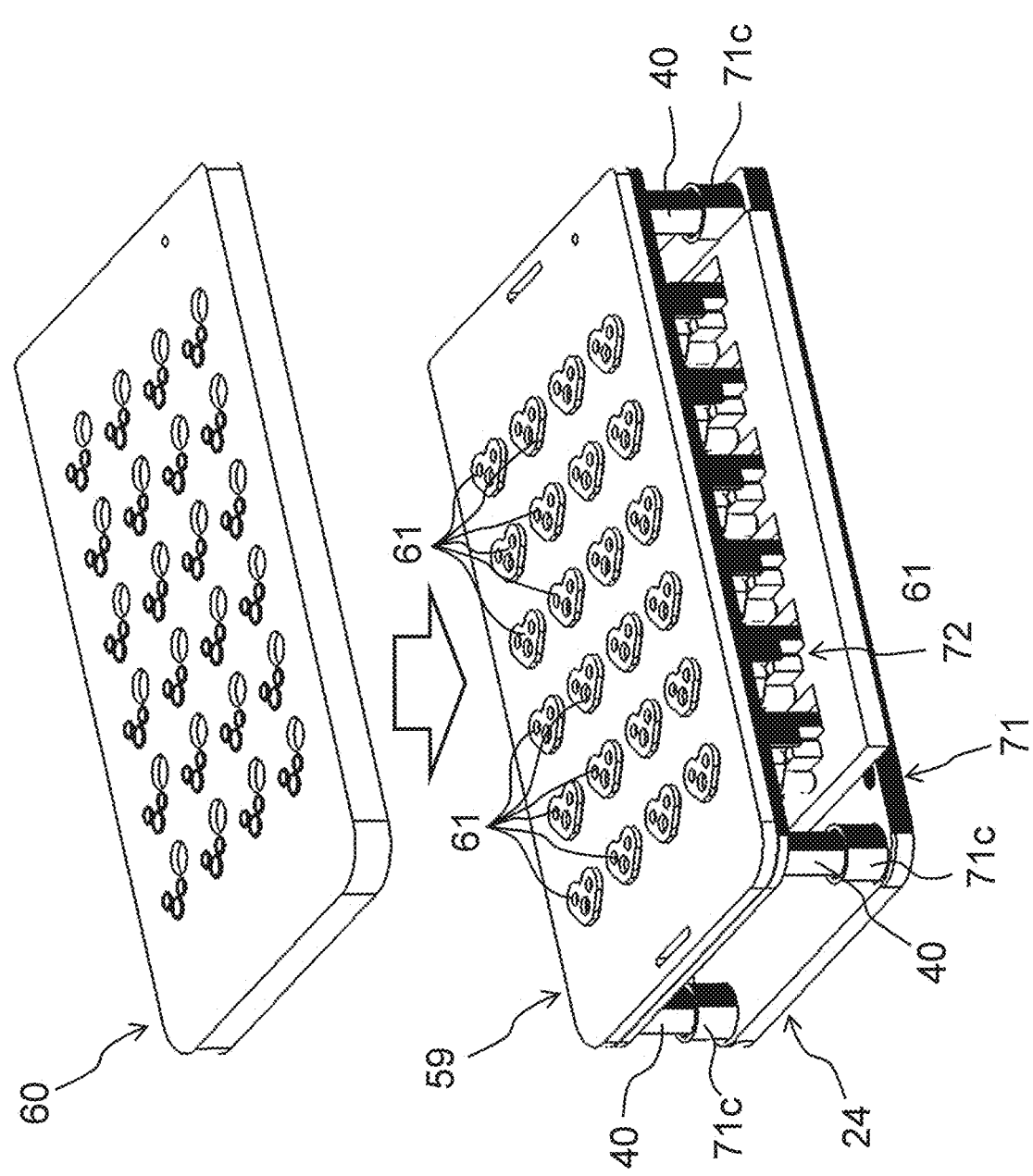
FIG. 27 is an oblique view showing the step of attaching a gasket sheet to the upper surface of the top plate shown in FIG. 25.

Finally, as shown in FIG. 27, the gasket sheet 60 is placed on the upper surface of the top plate 59.

This concludes the assembly of the sensor unit 27.

Embodiment 2

The configuration of the sensor unit according to another embodiment of the present invention will now be described with reference to the drawings.

Here, detailed description of members having the same function and shape as those of the members described in Embodiment 1 will be omitted, and the following description will focus on the differences from Embodiment 1.

The sensor unit 27 in this embodiment differs from the configuration of Embodiment 1 primarily in that a heater board (board) 62 is newly added to the configuration described in Embodiment 1.

Figure 29:
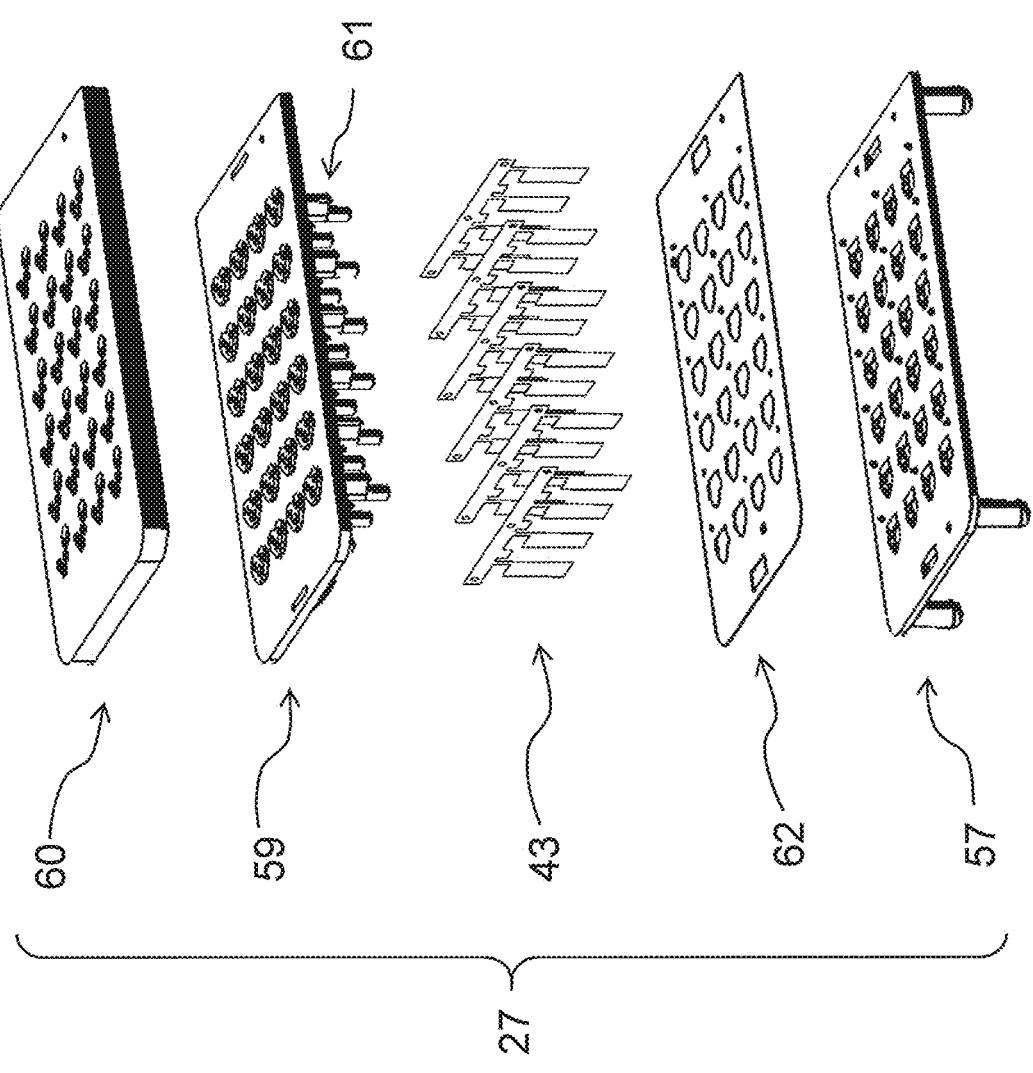
FIG. 29 is an exploded oblique view of the configuration of a sensor unit according to yet another embodiment of the present invention.

FIG. 29 shows the configuration of the sensor unit 27.

As shown in FIG. 29, the sensor unit 27 includes the bottom plate 57, the heater board (board) 62, the plurality of sensors 43, the top plate having the port 61 for supplying an additive, and a gasket sheet 60, in that order starting from the bottom.

Figures 30A, 30B:
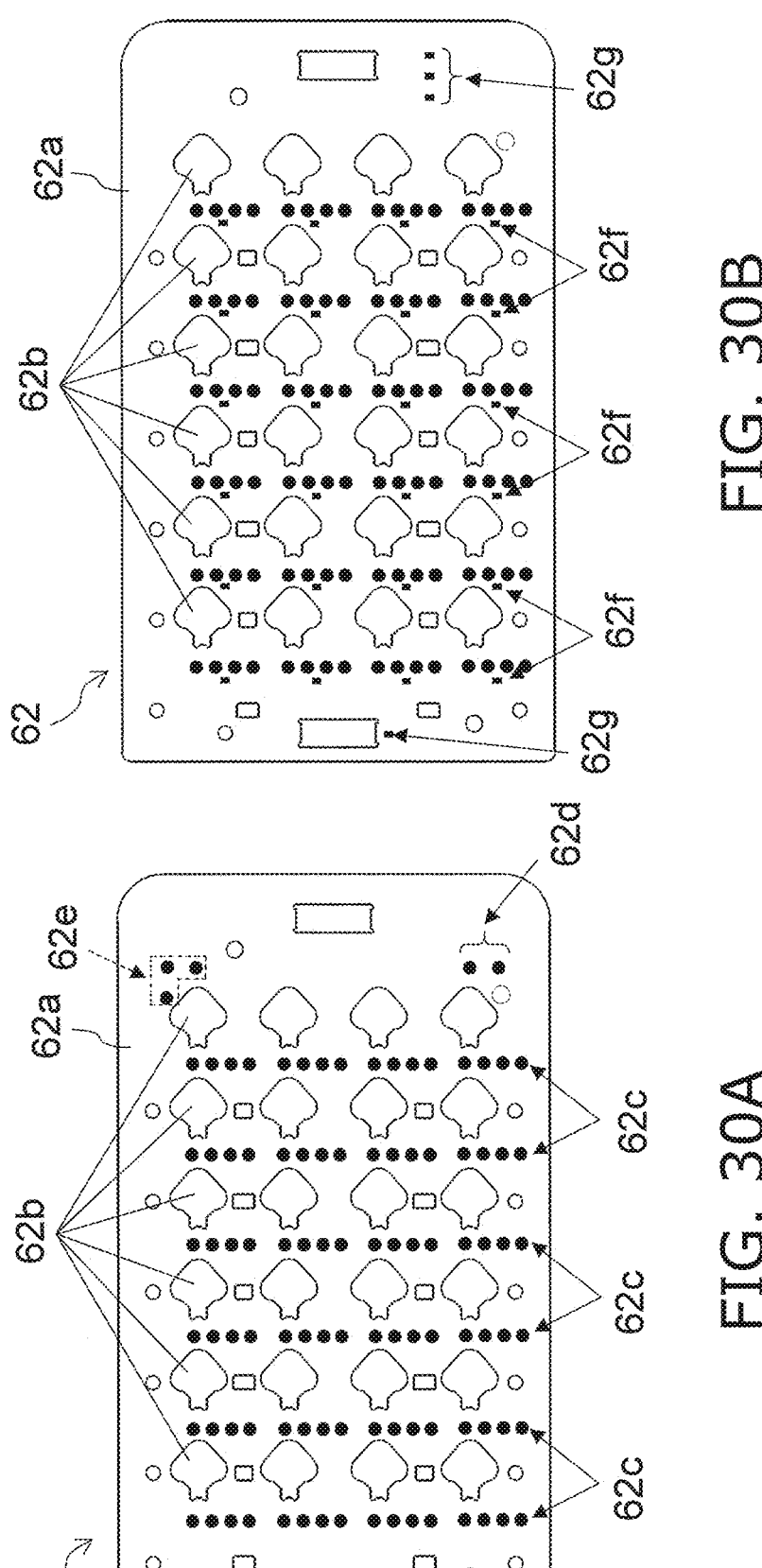
FIG. 30A is a plan view of the configuration on the upper surface side of a heater board included in the sensor unit in FIG. 29.
FIG. 30B is a plan view of the configuration of the lower surface side, which is the opposite side from that in FIG. 30A.

The heater board (board) 62 heats the contact portions 45c of the sensors 43 in order to prevent incorrect measurement by the sensors 43 due to dew condensation on the contact portions 45c in hot and humid environments. As shown in FIG. 29, the heater board 62 is a plate-like member and is disposed so as to be sandwiched between the bottom plate 57 and the top plate 59. As shown in FIGS. 30A and 30B, the heater board 62 has a board main body 62a, through-holes 62b, heating electrodes (heating units) 62c, electrodes 62d and 62e, resistance heating elements 62f, and thermistors 62g.

The board main body 62a is, for example, a flat glass epoxy board having high heat resistance, with a thickness of 0.2 mm. The board main body 62a has an upper surface (second surface) and a lower surface (first surface).

The through-holes 62b are openings formed to pass through the board main body 62a, and the sensors 43 disposed facing substantially vertically downward are inserted into these holes in the step of assembling the sensor unit 27 (discussed below).

The heating electrodes 62c are disposed in a set of four on the upper surface side of the board main body 62a, and transmit the heat generated by the resistance heating elements 62f to the contact portions 45c of the sensors 43 disposed at corresponding positions.

The electrodes 62d are power supply electrodes, and as shown in FIG. 30A, are provided at the end on the upper surface side of the board main body 62a. The power applied to the electrodes 62d heats the resistance heating elements 62f supplied through the wiring provided on the lower surface side.

The electrodes 62e are the electrodes for the thermistors 62g, and are provided on the upper surface side of the board main body 62a as shown in FIG. 30A. Power is supplied through the electrodes 62e to the thermistors 62g provided on the lower surface side.

The resistance heating elements 62f are, for example, metal-based heating elements such as Ni—Cr, Fe—Cr—Al, molybdenum, tungsten, or platinum, and generate Joule heat using electricity as an energy source. The resistance heating elements 62f are disposed at positions adjacent to the heating electrodes 62c on the lower surface (first surface) side, and one resistance heating element 62f is provided to a set of four heating electrodes 62c.

As shown in FIG. 30B, the thermistors 62g are provided near both ends on the lower surface side, and measure the ambient temperature of the space above the culture medium.

The heater board 62 is controlled by the control unit 4 (see FIG. 1 in Embodiment 1) so that the increase in the ambient temperature above the culture medium is kept to 0.5° C. or less, for example. Also, the heater board 62 is set so that the board temperature rises by about 2° C. The heater board 62 controls the amount of current of the resistance heating elements 62*f* so that the temperature information sensed by the thermistors 62*g* approaches a preset target temperature. More specifically, the initial ambient temperature sensed by the thermistors 62*g* is read, and current is supplied to the resistance heating elements 62*f* so that the ambient temperature rises by 2 degrees. The current value supplied at this point is set to a specific value in advance.

As a result, when the heater board 62 heats the contact portions 45*c* of the sensors 43 via the heating electrodes 62*c*, this prevents the sensors 43 from becoming unusable due to an electrical short even in a hot and humid environment.

Also, there is the risk that the heat generated in the heater board 62 will be transferred to the well plate 25 containing the culture medium through the bottom plate 57 disposed on top.

In this embodiment, since the bottom plate 57 is formed from a material having excellent heat insulation properties, such as acrylonitrile butadiene (ABS), polystyrene (PS), or another such resin, this reduces the effect that the heat generated in the heater board 62 has on the culture medium.

Sensor Unit 27 Assembly Step

Here, the step of assembling the sensor unit 27, including the step of attaching the sensors 43 to the bottom plate 57, will now be described with reference to the drawings.

Figure 31:
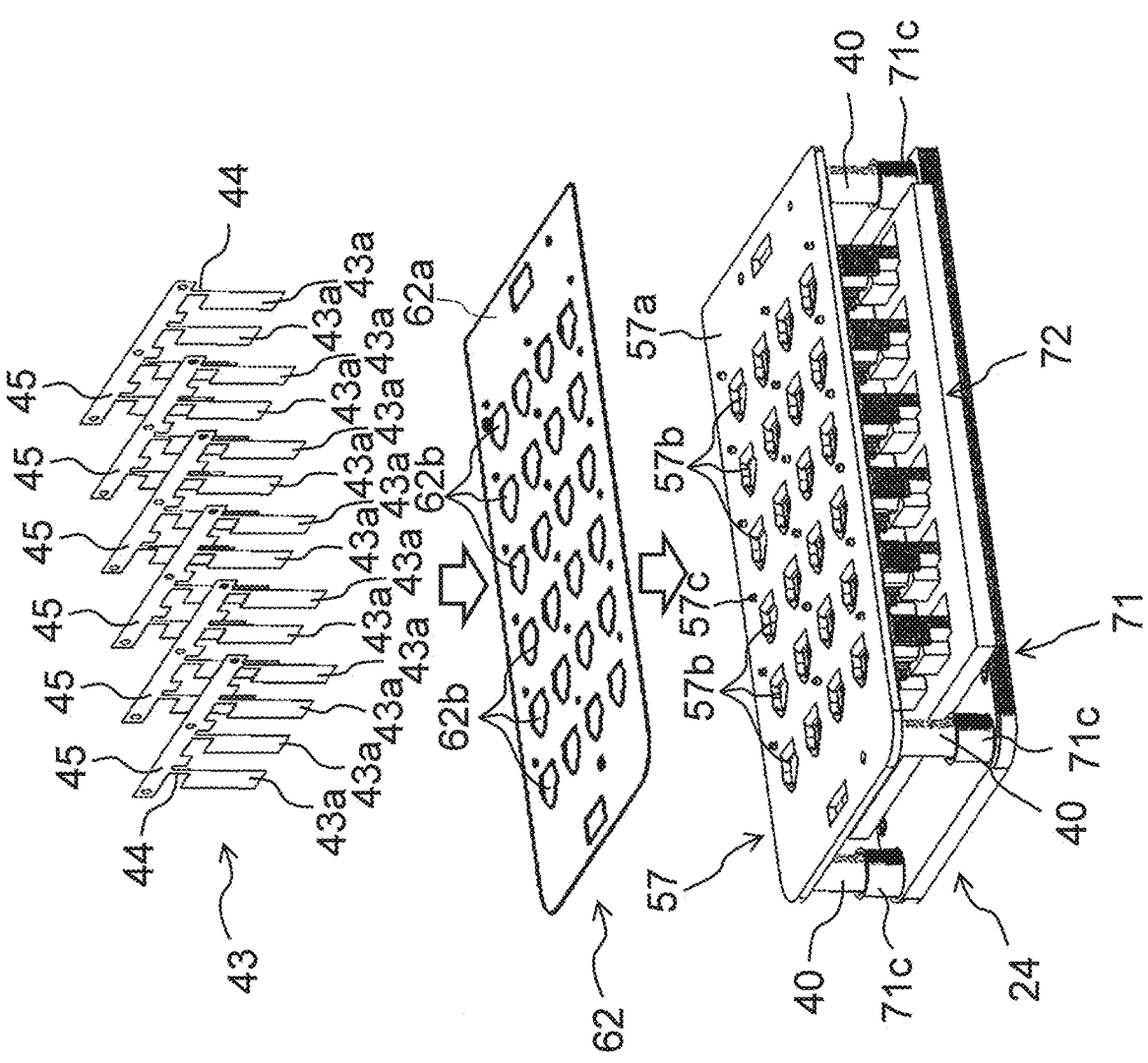
FIG. 31 is an oblique view showing a state in which the sensors are inserted into the through-holes in the heater board and the bottom plate in the assembly of the sensor unit in FIG. 29.

In the step of assembling the sensor unit 27, as shown in FIG. 31, six sets (4×6=24) of sensors 43 are inserted into the through-holes 62*b* of the board 62 and the through-holes 57*b* formed in the bottom plate 57 in a state in which the bottom plate 57 is disposed on the upper surface side of the sensor fixing jigs 71 and 72.

Figure 32:
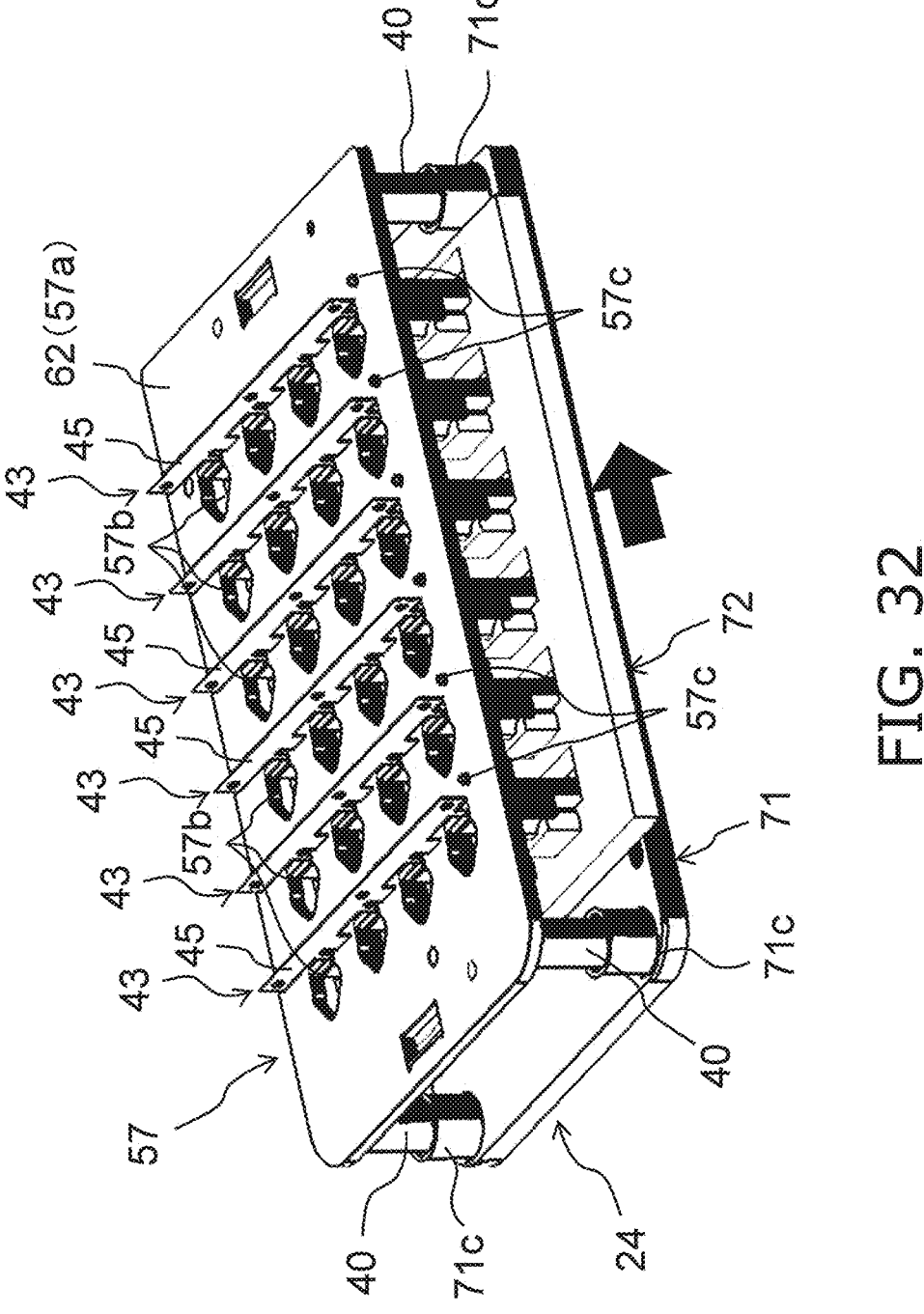
FIG. 32 is an oblique view showing a state in which the main bodies of the sensors are held by sliding the sensor fixing jig in the assembly of the sensor unit in FIG. 29.

When the sensors 43 are inserted into the through-holes 62*b* of the heater board 62 and the through-holes 57*b* of the bottom plate 57, the contact portions 46 of the sensors 43 come into contact with the upper surface of the board main body 62*a* of the heater board 62 (bottom plate 57), as shown in FIG. 32.

At this point, as discussed above, since the contact portions 46 are disposed along the straight line of the bending line 44*a*, the bending portions 44 can be bent along the bending line 44*a*, with the contact portions 46 as the starting point, in a state in which the contact portions 46 are in contact with the upper surface of the bottom plate 57.

Consequently, the sensors 43 bent along the bending line 44*a* with the contact portions 46 as the starting point are accurately disposed facing downward from the through-holes 62*b* in the heater board 62, so the positional accuracy of the sensors 43 with respect to the wells 25*a* can be improved.

Also, as shown in FIG. 32, the sensor fixing jig 72 slides in the direction of the arrow in the drawing (to the right) with respect to the sensor fixing jig 71 in a state in which the sensors 43 have been inserted into the through-holes 62*b* of the heater board 62 and the through-holes 57*b* of the bottom plate 57.

Consequently, the main bodies 43*a* of the sensors 43 are accurately positioned by the sensor fixing jigs 71 and 72.

Figure 33:
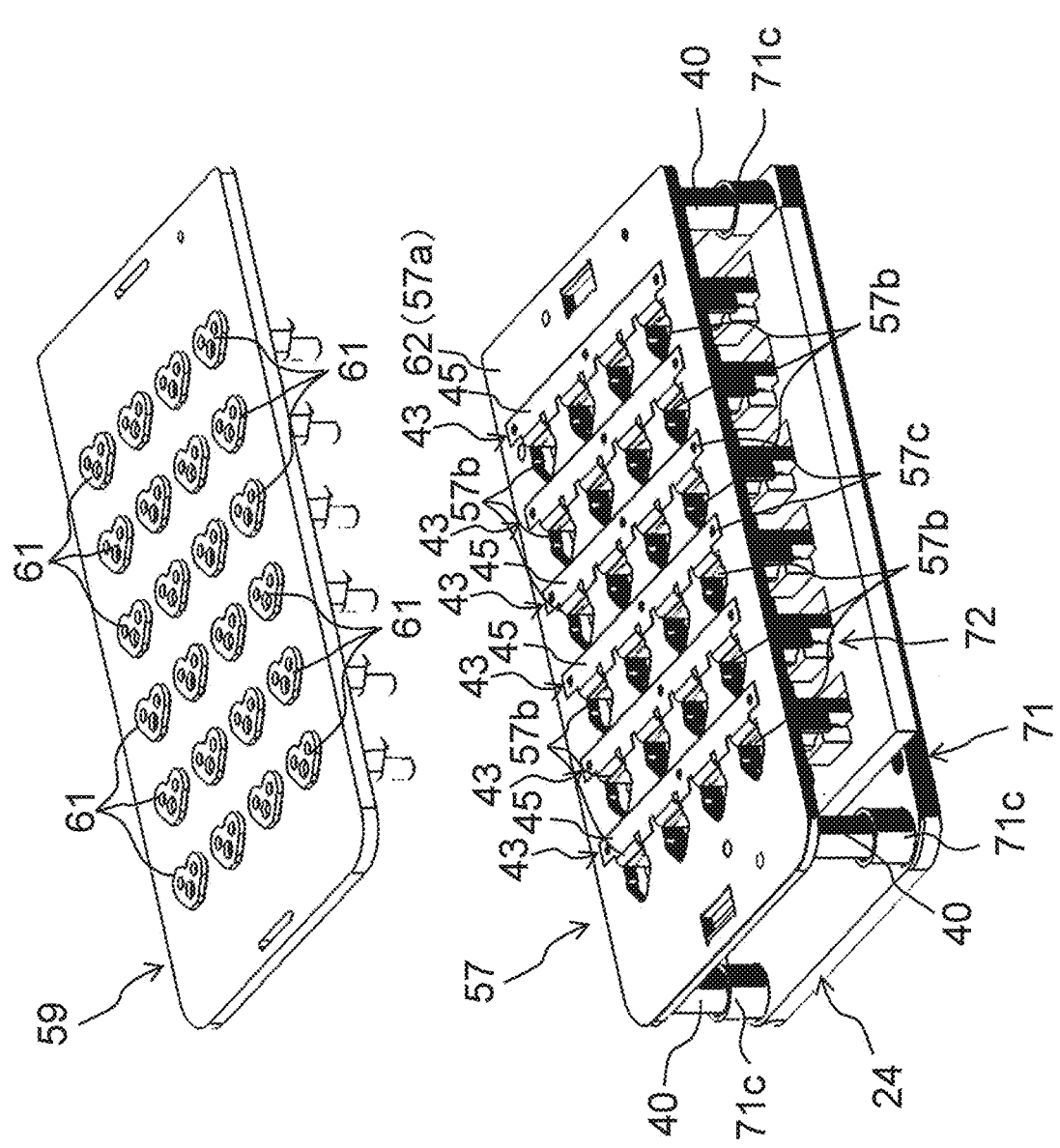
FIG. 33 is an oblique view showing the step of bending the linking portion from the state shown in FIG. 32 and attaching the top plate thereon.

Next, while the main bodies 43*a* of the sensors 43 are still held by the sensor fixing jigs 71 and 72, the linking portion 45 is bent substantially parallel to the upper surfaces of the heater board 62 and the bottom plate 57 as shown in FIG. 33.

The bending of the linking portion 45 may be performed manually or by using a tool such as a bending jig, or may be automatically performed by a robot hand or the like.

At this point, as discussed above, the main bodies 43*a* of the sensors 43 are held by the sensor fixing jigs 71 and 72 in a state of having been inserted into the through-holes 62*b* of the heater board 62 and the through-holes 57*b* of the bottom plate 57. Therefore, when the bending portions 44 are bent along the bending line 44*a* with the contact portions 46 as the starting point, the linking portion 45 is bent substantially parallel to the upper surfaces of the heater board 62 and the bottom plate 57, as shown in FIG. 34.

Figure 34:
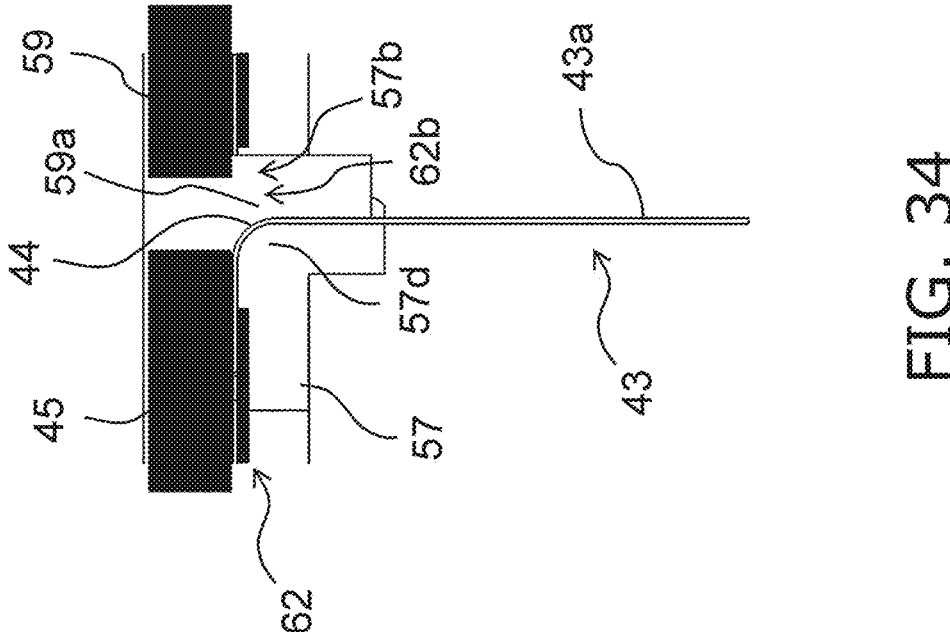
FIG. 34 is a cross-sectional view of a sensor held between the bottom plate (heater board) and the top plate.

Furthermore, in the state shown in FIG. 34, three through-holes 57*b* and three prongs 57*c* are disposed for one set of four sensors 43 on the upper surface of the plate portion 57*a* of the bottom plate 57.

Next, the heater board 62 and the top plate 59 are disposed on top of the bottom plate 57 in a state in which the linking portion 45 is bent.

At this point, the sensors 43 disposed so as to be sandwiched between the lower surface of the top plate 59 and the upper surface of the heater board 62 (bottom plate 57) are held between support portions 57*d* on the top plate 59 side and the pressing portions 59*a* on the bottom plate 57 side, as shown in FIG. 34.

That is, the support portions 57*d*, which support the lower sides of the bending portions 44 of the sensors 43, are provided at the opening edges of the through-holes 57*b* in the bottom plate 57. The portion of the top plate 59 that is opposite the support portions 57*d* is provided with the pressing portions 59*a* that press the upper sides of the bending portions 44 of the sensors 43 downward.

Consequently, the upper surfaces of the sensors 43 are supported by the pressing portions 59*a*, and the lower surfaces are supported by the support portions 57*d* provided on the upper surface side of the bottom plate 57.

As shown in FIG. 34, a support portion 57*d* has an upper surface curved portion shape that includes a curved upper surface. Also, as shown in FIG. 34, the pressing portion 59*a* has a lower surface curved portion shape that includes a curved lower surface.

Consequently, as shown in FIG. 34, when the sensor 43 is sandwiched between the top plate 59 and the heater board 62 (bottom plate 57), the bending portion 44 of the sensor 43 is held in a state of being sandwiched from above and below by the support portion 57*d* and the pressing portion 59*a*.

Therefore, since the bending angle of the sensor 43 is accurately defined, the sensing unit 43*b* provided at the lower end portion of the main body 43*a* of the sensor 43 is disposed in a stable state.

As a result, the immersion depth of the sensing units 43*b* immersed in the culture medium in the wells 25*a* included in the well plate 25 can be controlled accurately, which improves the sensing accuracy.

Finally, the gasket sheet 60 is placed on the upper surface of the top plate 59 to complete the assembly of the sensor unit 27.

As discussed above, the sensor unit 27 of this embodiment has the sensors 43 for measuring the components of the culture medium in the well plate 25, and comprises the sensor 43 and the heater board 62. The sensors 43 each have a main body 43*a*, a sensing unit 43*b* that is disposed on the main body 43*a* and is immersed in the culture medium, and a contact portion 45*c* that is electrically connected to the sensing unit 43*b* and measures the components of the culture medium. The heater board 62 heats the contact portion 45*c* of the sensor 43.

Consequently, the contact portion 45*c* of the sensor is heated by applying the heat generated in the heater board 62 to the contact portion 45*c*, and this prevents leakage current from flowing between adjacent contact portions 45*c* due to moisture that has condensed near the contact portions 45*c*.

As a result, even in a hot and humid environment, it is possible to prevent the sensor from becoming unusable due to an electrical short caused by dew condensation around the contact portion 45c, and this ensures stable electrical connection.

Embodiment 3

The configuration of the sensor unit 127 according to yet another embodiment of the present invention will now be described with reference to the drawings.

Figure 35:
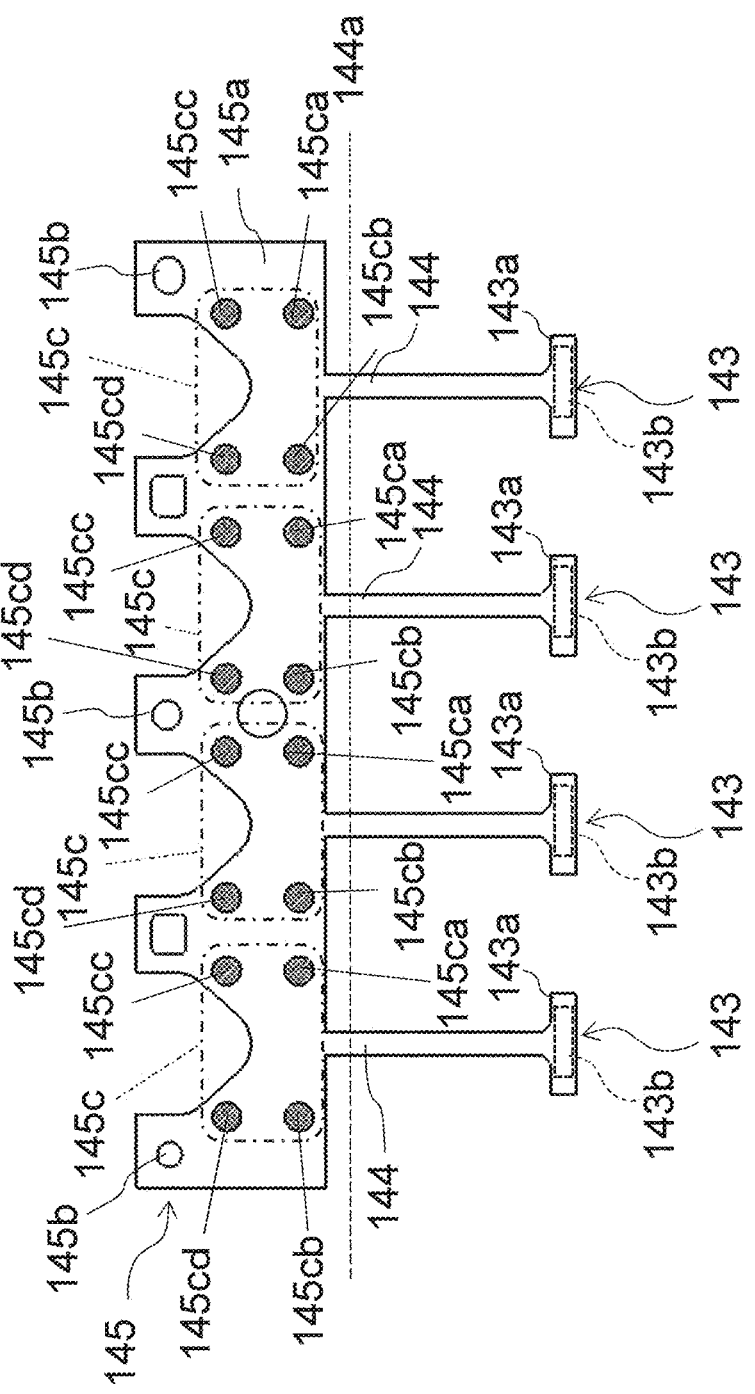
FIG. 35 is an oblique view of the configuration of sensors included in a sensor unit according to still another embodiment of the present invention.

With the sensor unit 127 in this embodiment, as shown in FIG. 35, the sensors 143 have a different form from that of the sensors 43 in Embodiment 2 above, and also differs from Embodiment 2 in the configuration of the heater board 162.

In this embodiment, those members having the same function and configuration as in Embodiment 2 are numbered the same and will not be described again.

As shown in FIG. 35, the sensors 143 included in the sensor unit 127 of this embodiment are configured, for example, by sputtering a gold electrode layer on the upper surface of a PET (polyethylene terephthalate) film, which is a resin material. The sensors 143 each have a main body 143a, a sensing unit 143b, a bending portion 144, and a linking portion 145, as shown in FIG. 35.

The main body 143a is a substantially rectangular flat member, and is linked at its upper end portion to the bending portion 144.

The sensing unit 143b is provided on the surface of the lower part of the substantially rectangular main body 143a, and includes measurement electrodes (a working electrode, a counter electrode, and a reference electrode). A specific voltage is applied to the measurement electrodes of the sensing unit 143b immersed in the culture medium contained in the well 25a, and the concentration of a specific component of the culture medium is electrochemically measured.

Each measurement electrode included in the sensing unit 143b is formed by evaporating and dividing an electrode layer with a laser.

The method for measuring the concentration of glucose contained in the culture medium is as described in Embodiments 1 and 2 above.

The bending portion 144 is the portion that links the main body 143a and the linking portion 145, and is bent substantially at a right angle along the bending line 144a. As a result, the linking portion 145 is disposed substantially perpendicular to the main body 143a.

Also, the bending portion 144 has a narrower width (the dimension in the left and right direction in the drawing) than the main body 143a. That is, the bending portion 144 is formed as if cut out to leave a portion thinner than the main body 143a. Consequently, when the linking portion 145 is bent with respect to the main body 143a, less force is required for bending along the bending line 144a, so the linking portion 145 can be easily bent.

The linking portion 145 links the upper end portions of the main bodies 143a of four sensors 143 to each other via the bending portions 144. The linking portion 145 has a main body 145a, positioning holes 145b, four contact portions 145c.

The main body 145a is disposed along a direction substantially perpendicular to the lengthwise direction of the main body 143a of the sensor 143, which has a substantially inverted T shape, and the upper end portions of the main bodies 143a of the four sensors 143 are linked together via the bending portions 144.

The positioning holes 145b are latched in a state in which the prongs provided on the bottom plate 57 side have been inserted, just as in the step of assembling the sensor unit 27 in Embodiments 1 and 2 above. This positions the sensors 143 with respect to the bottom plate 57.

The contact portions 145c are disposed in a set of four corresponding to the sensing unit 143b of a single sensor 143, and are electrically connected to the measurement electrodes (working electrode, counter electrode, and reference electrode) included in the sensing unit 143b disposed at the lower part of the main body 143a of the sensor 143.

More precisely, as shown in FIG. 35, the contact portions 145c each include a first working electrode contact portion 145ca, a second working electrode contact portion 145cb, a counter electrode contact portion 145cc, and a reference electrode contact portion 145cd, which are disposed at the four corners of a substantially rectangular shape.

The contact portions 145ca and 145cb for the first and second working electrodes are disposed a specific distance apart, in the lower row among the four contacts included in the contact portion 145c.

The counter electrode contact portion 145cc and the reference electrode contact portion 145cd are disposed in the upper row among the four contacts included in the contact portion 145c.

The first working electrode contact portion 145ca is a contact corresponding to the measurement electrode (first working electrode) of the sensing unit 143b, and is provided primarily for measuring the concentration of glucose in the culture medium, for example.

The second working electrode contact portion 145cb is a contact corresponding to the measuring electrode (second working electrode) of the sensing unit 143b, and is provided primarily for measuring the concentration of lactic acid in the culture medium, for example.

The counter electrode contact portion 145cc is a contact corresponding to the measurement electrode (counter electrode) of the sensing unit 143b.

The reference electrode contact portion 145cd is a contact corresponding to the measurement electrode (reference electrode) of the sensing unit 143b.

With the sensors 143 included in the sensor unit 127 of this embodiment, as shown in FIG. 35, the contact portions 145ca and 145cb for the two working electrodes (first and second working electrodes) are disposed at positions that are apart from each other.

Consequently, it is less likely that the sensors 143 will become unable to perform measurement due to the flow of leakage current caused by short-circuiting attributable to moisture condensation or the like on the contact portions 145ca and 145cb for the two working electrodes (first and second working electrodes).

Also, the distance between the first working electrode contact portion 145ca and the second working electrode contact portion 145cb is greater than the distance to the counter electrode contact portion 145cc or the distance to the reference electrode contact portion 145cd.

As a result, since the contact portions 145ca and 145cb for the two working electrodes (first and second working electrodes) are spaced apart more than their distance to the other two contact portions 145cc and 145cd, it is less likely that the sensors 143 will become incapable of measurement due to a short circuit caused by moisture condensation or the like between the contact portions 145ca and 145cb for the working electrodes (first and second working electrodes) that would produce leakage current.

The sensors 143 shown in FIG. 35 are used in a state of being sandwiched between the top plate 59 and the bottom plate 157 together with the heater board (board) 162, as mentioned above.

The heater board (board) 162 is provided in order to heat the contact portions 145c of the sensors 143 so as to prevent measurement failure of the sensor 143 due to condensation in the contact portions 145c (the contact portions 145ca and 145cb for the first and second working electrodes, the counter electrode contact portion 145cc, and the reference electrode contact portion 145cd) in a hot and humid environment.

Figures 36A, 36B:
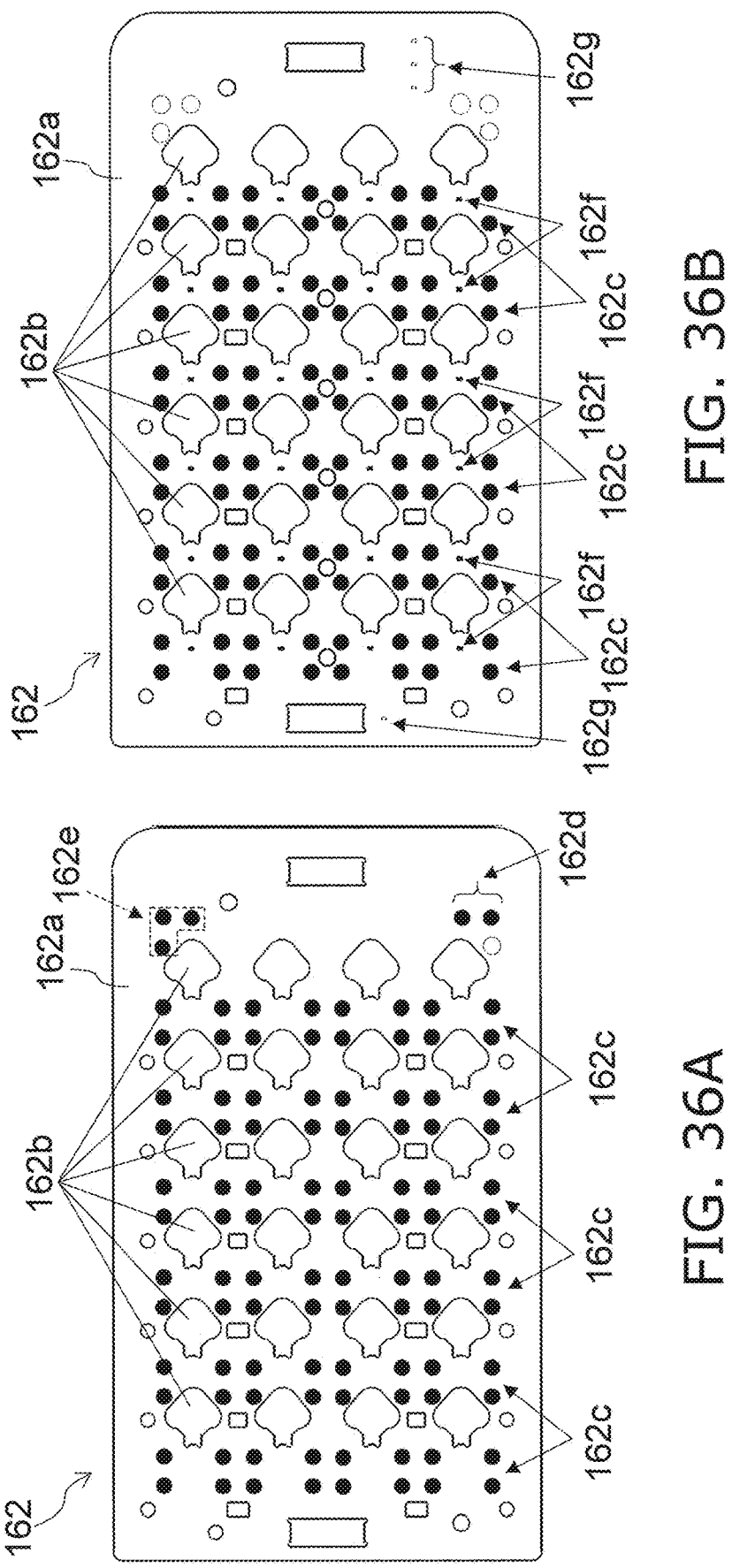
FIG. 36A is a plan view of the configuration on the upper surface side of the heater board included in the sensor unit.
FIG. 36B is a plan view of the configuration on the lower surface side, which is the opposite side from that in FIG. 36A.

As shown in FIGS. 36A and 36B, the heater board 162 has a board main body 162a, through-holes 162b, heating electrodes (heating units) 162c, electrodes 162d and 162e, resistance heating elements 162f, and thermistors 162g.

The board main body 162a is, for example, a flat glass epoxy board having high heat resistance, with a thickness of 0.2 mm. The board main body 162a has an upper surface (second surface) and a lower surface (first surface).

The through-holes 162b are openings formed to pass through the board main body 162a, and the sensors 143 disposed facing substantially vertically downward are inserted into these holes in the step of assembling the sensor unit 127.

The heating electrodes 162c are disposed in a set of four on the upper surface side of the board main body 162a, and transmit the heat generated by the resistance heating elements 162f to the contact portions 145c of the sensors 143 disposed at corresponding positions (the contact portions 145ca and 145cb for the two working electrodes, the counter electrode contact portion 145cc, and the reference electrode contact portion 145cd).

The electrodes 162d are power supply electrodes, and as shown in FIG. 36A, are provided at the end on the upper surface side of the board main body 162a. The power applied to the electrodes 162d heats the resistance heating elements 162f supplied through the wiring provided on the lower surface side.

The electrodes 162e are the electrodes for the thermistors 162g, and are provided on the upper surface side of the board main body 162a as shown in FIG. 36A. Power is supplied through the electrodes 162e to the thermistors 162g provided on the lower surface side.

The resistance heating elements 162f are, for example, heating elements based on a metal such as Ni—Cr, Fe—Cr—Al, molybdenum, tungsten, or platinum, and generate Joule heat using electricity as the energy source. The resistance heating elements 162f are disposed at positions adjacent to the heating electrodes 162c on the lower surface (first surface) side, and one resistance heating element 162f is provided to a set of four heating electrodes 162c.

As shown in FIG. 36B, the thermistors 162g are provided near both ends on the lower surface side, and measure the ambient temperature of the space above the culture medium.

Figure 37:
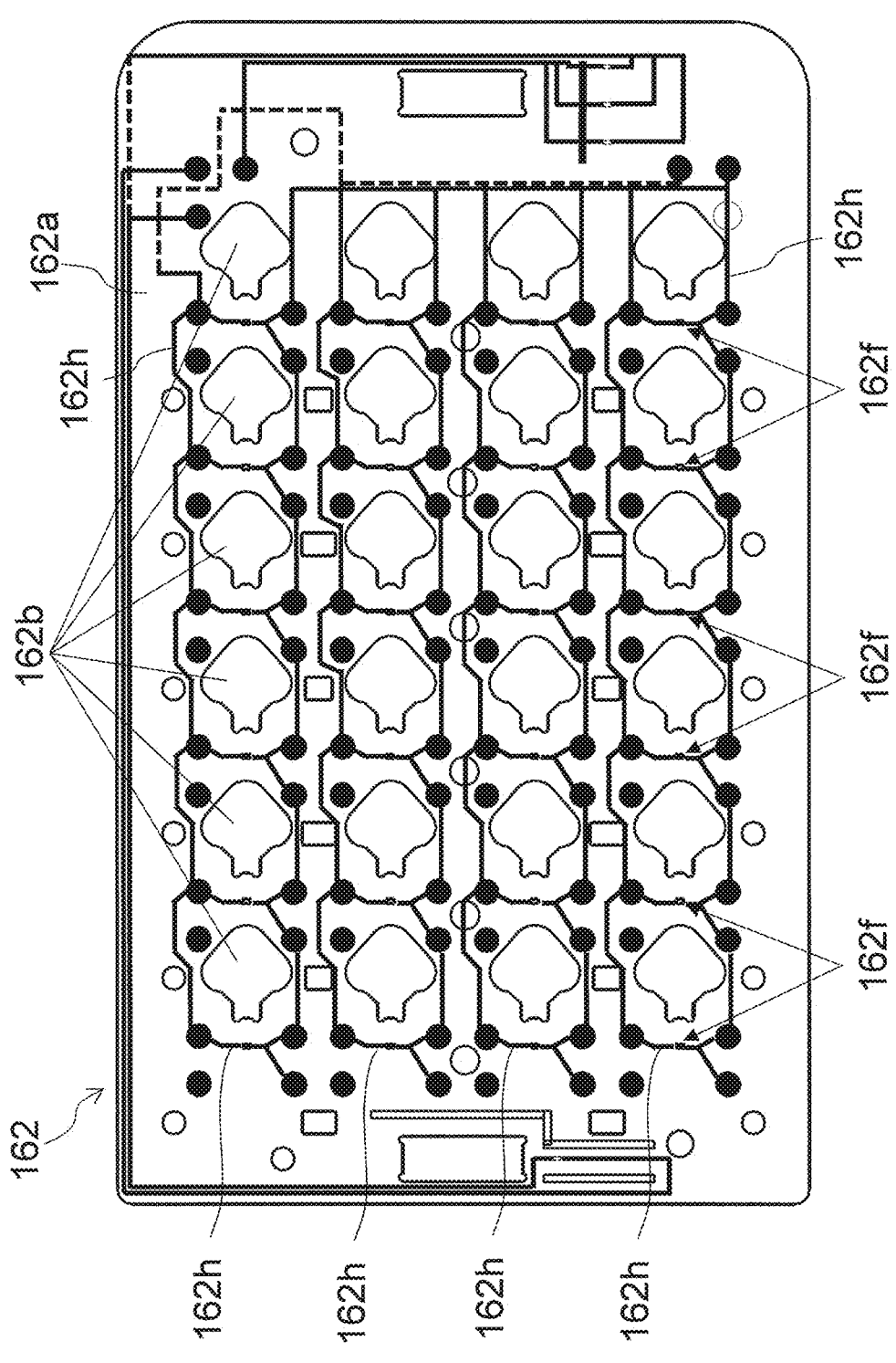
FIG. 37 is a plan view of the detailed configuration including wiring disposed on the lower surface side of the heater board in FIG. 36B.

As shown in FIG. 37, wires 162h are disposed on the lower surface side of the heater board 162 to connect the power supply electrodes 162d and the heating electrodes 162c. With these wires 162h, one set of four heating electrodes 162c branches into four rows connected in parallel with each other, and six sets are disposed in each row.

Consequently, by applying voltage to the power supply electrodes 162d, power can be supplied to the heating electrodes 162c and the resistance heating elements 162f in each row.

Figures 38A, 38B:
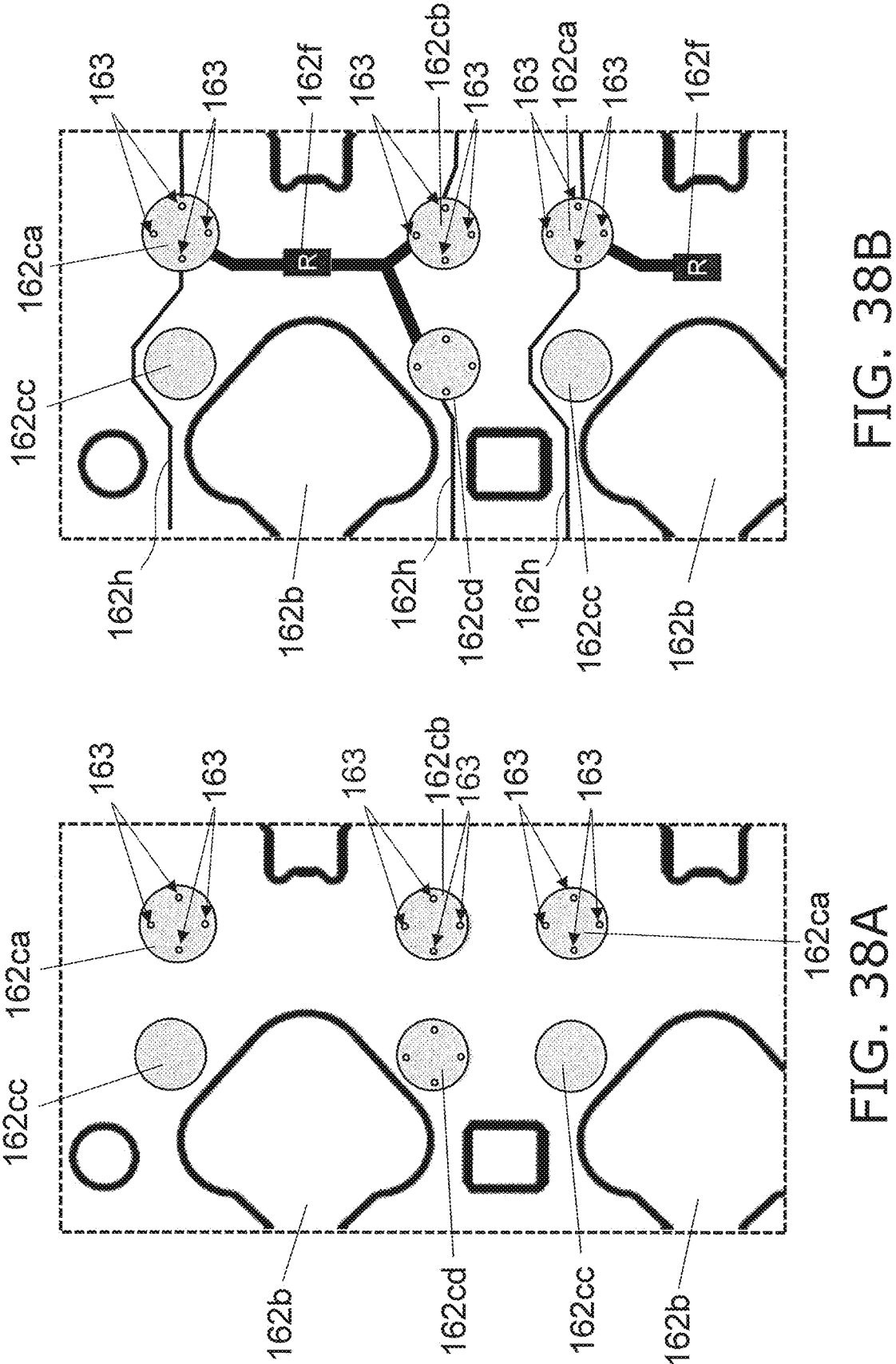
FIG. 38A is a detail plan view of a portion of the upper surface side of the heater board in FIG. 36A.
FIG. 38B is a detail plan view of a portion of the lower surface side of the heater board in FIG. 36B.

As shown in FIG. 38A, the heating electrodes 162c include heating electrodes 162ca for the first working electrode, heating electrodes 162cb for the second working electrode, heating electrodes 162cc for the counter electrode, and heating electrodes 162cd for the reference electrode.

The heating electrodes 162ca for the first working electrode are disposed opposite the positions of the sensor 143 corresponding to the first working electrode contact portions 145ca, and heat the contact portions 145ca by coming into contact with the contact portions 145ca.

The second working electrode heating electrodes 162cb are disposed opposite the second working electrode contact portions 145cb of the sensors 143, and heat the contact portions 145cb by coming into contact with the contact portions 145cb.

The counter electrode heating electrodes 162cc are disposed opposite the counter electrode contact portions 145cc of the sensors 143, and heat the contact portions 145cc by coming into contact with the contact portions 145cc.

The reference electrode heating electrodes 162cd are disposed opposite the reference electrode contact portions 145cd of the sensors 143, and heat the contact portions 145cd by coming into contact with the contact portions 145cd.

Here, four vias 163 are formed for each heating electrode 162ca so as to pass through the heating electrode 162ca to the upper and lower surfaces of the heater board 162, as shown in FIG. 38A. Similarly, four vias 163 are also formed for each heating electrode 162cb for the second working electrode and each heating electrode 162cd for the reference electrode.

The vias 163 are, for example, through-holes with a diameter of 0.3 mm, and are subjected to filled plating.

Consequently, the heating electrodes 162ca, 162cb, and 162cd can transfer heat from the lower surface side to the upper surface side of the heater board 162 through the vias 163.

On the lower surface side of the heater board 162, as shown in FIG. 38B, the heating electrodes 162ca to 162cd are electrically connected by the wires 162h. Resistance heating elements 162f that are connected to the heating electrodes 162ca and 162cb via the wires 162h are disposed between the heating electrodes 162ca and 162cb for the first and second working electrodes, as shown in FIG. 38B.

As a result, heat is efficiently transferred through the wires 162h to the heating electrodes 162ca and 162cb for the first and second working electrodes disposed near the resistance heating elements 162f.

The heater board 162 is controlled by the control unit 4 (see FIG. 1 of Embodiment 1) so that the increase in the ambient temperature above the culture medium is 0.5° C. or less, for example. The heater board 162 is set so that the board temperature rises by about 2° C. The heater board 162 controls the amount of current to the resistance heating elements 162f so that the temperature information sensed by the thermistors 162g approaches a preset target temperature. More specifically, the ambient temperature in the initial state sensed by the thermistors 162g is read, and current is supplied to the resistance heating elements 162f so that the ambient temperature rises by 2 degrees. The amount of current supplied at this time is set to a specific value in advance.

Consequently, the heater board 162 heats the contact portions 145c of the sensors 143 via the heating electrodes 162c, and this prevents the sensors 143 from becoming unusable due to electrical short-circuiting, even in a hot and humid environment.

Figures 39A, 39B:
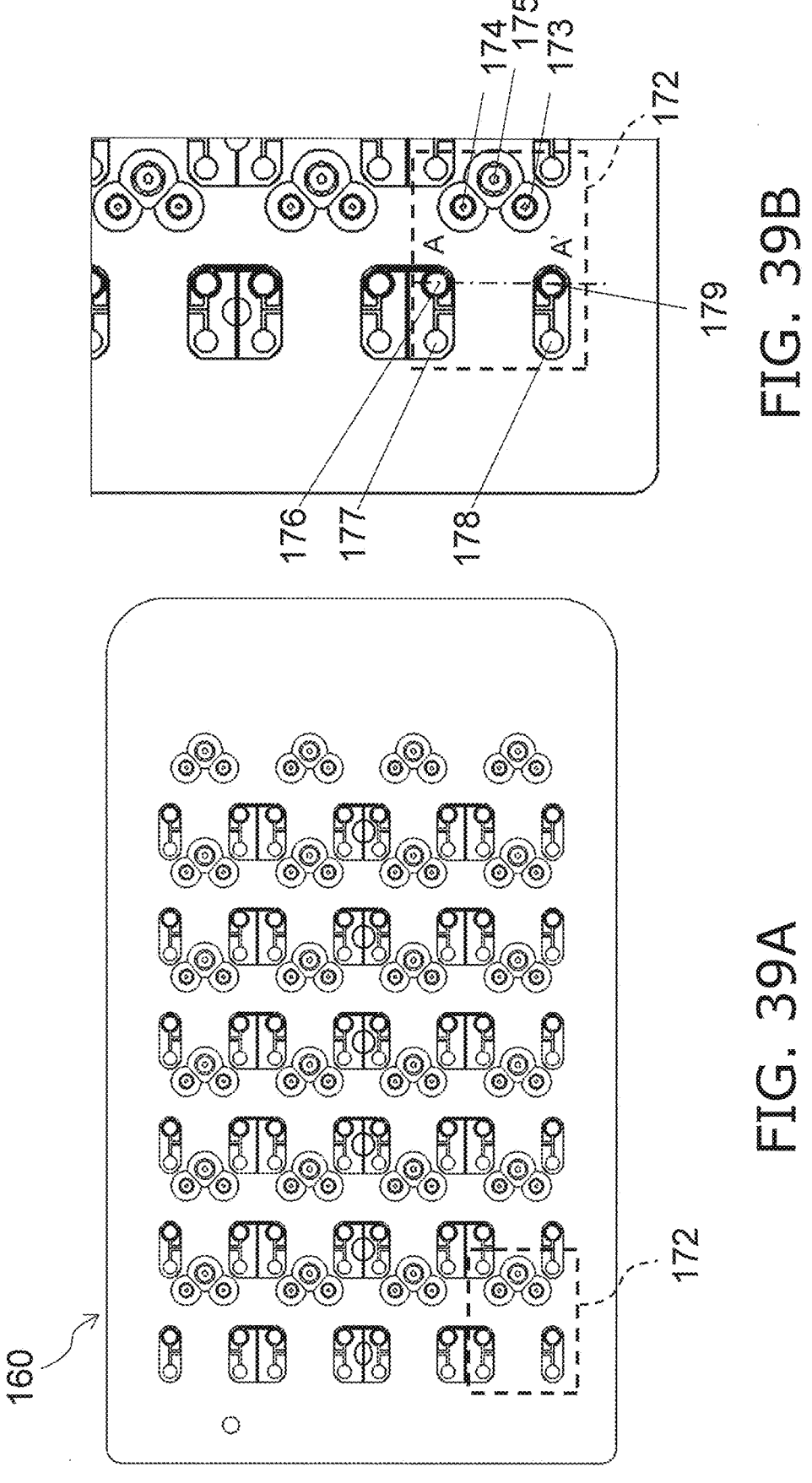
FIG. 39A is a plan view of the configuration on the upper surface side of a gasket sheet disposed on the uppermost surface of the sensor unit.
FIG. 39B is a detail plan view of a portion thereof.

Here, a plurality of port input/output units 172, which are disposed in close contact with the upper surface of a plurality of ports 61 (see FIG. 29), are disposed on the upper surface of the gasket sheet 160 disposed on the uppermost surface of the assembled sensor unit 127, as shown in FIG. 39A.

The port input/output units 172 each has an additive addition unit A addition port (top opening) 173, an additive addition unit B addition port (top opening) 174, and an stirring member air discharge suction port 175. Also, the port input/output units 172 have through-holes for connecting to the contact portions 145c of the sensors 143. As shown in FIG. 39B, four through-holes are formed, namely, a through-hole 176 for a first working electrode pad, a through-hole 177 for a counter electrode pad, a through-hole 178 for a reference electrode pad, and a through-hole 179 for a second working electrode pad.

Figure 40:
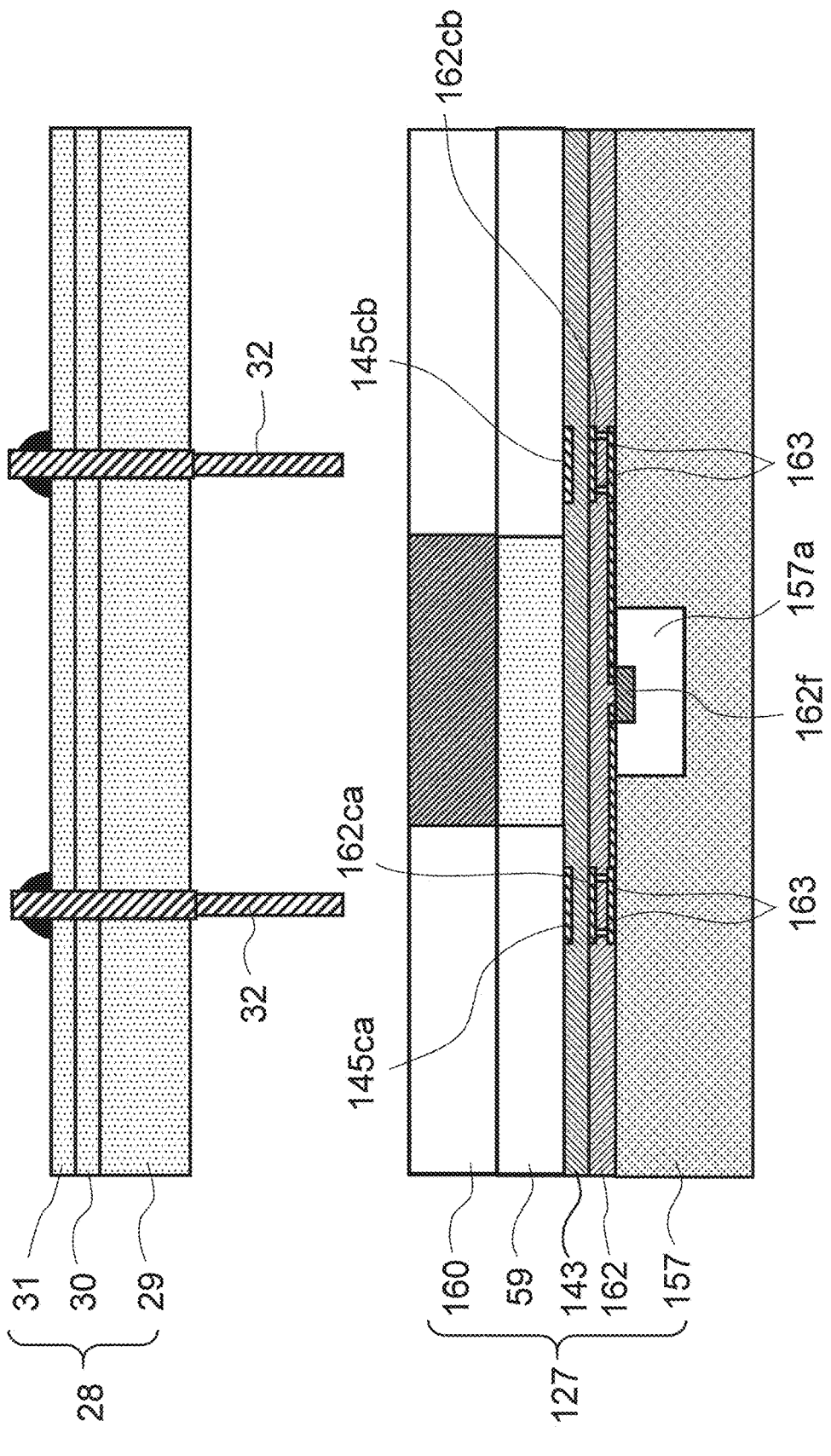
FIG. 40 is a cross-sectional view along the A-A' line in FIG. 39B.

The plurality of port input/output units 172 are disposed on the upper surface of the gasket sheet 160 as described with reference to FIGS. 39A and 39B. FIG. 40 shows the state before the board unit 28 is assembled from above onto the upper surface of the sensor unit 127 with the gasket sheet 160 disposed on the upper surface thereof.

Before the board unit 28 is incorporated into the sensor unit 127, an additive is preloaded through the additive addition part 173.

The connecting portions 32 provided extending downward from the board 31 protrude downward from the lower surface of the board unit 28, and are electrically connected to the contact portions 145ca and 145cb for the first and second working electrodes of the sensors 143 through through-holes 178 for the reference electrode pad and through-holes 179 for the second working electrode pad, as shown in FIG. 39B.

This electrical connection structure is the same on the counter electrode pad through-hole 177 side and the reference electrode pad through-hole 178 side.

Figure 41:
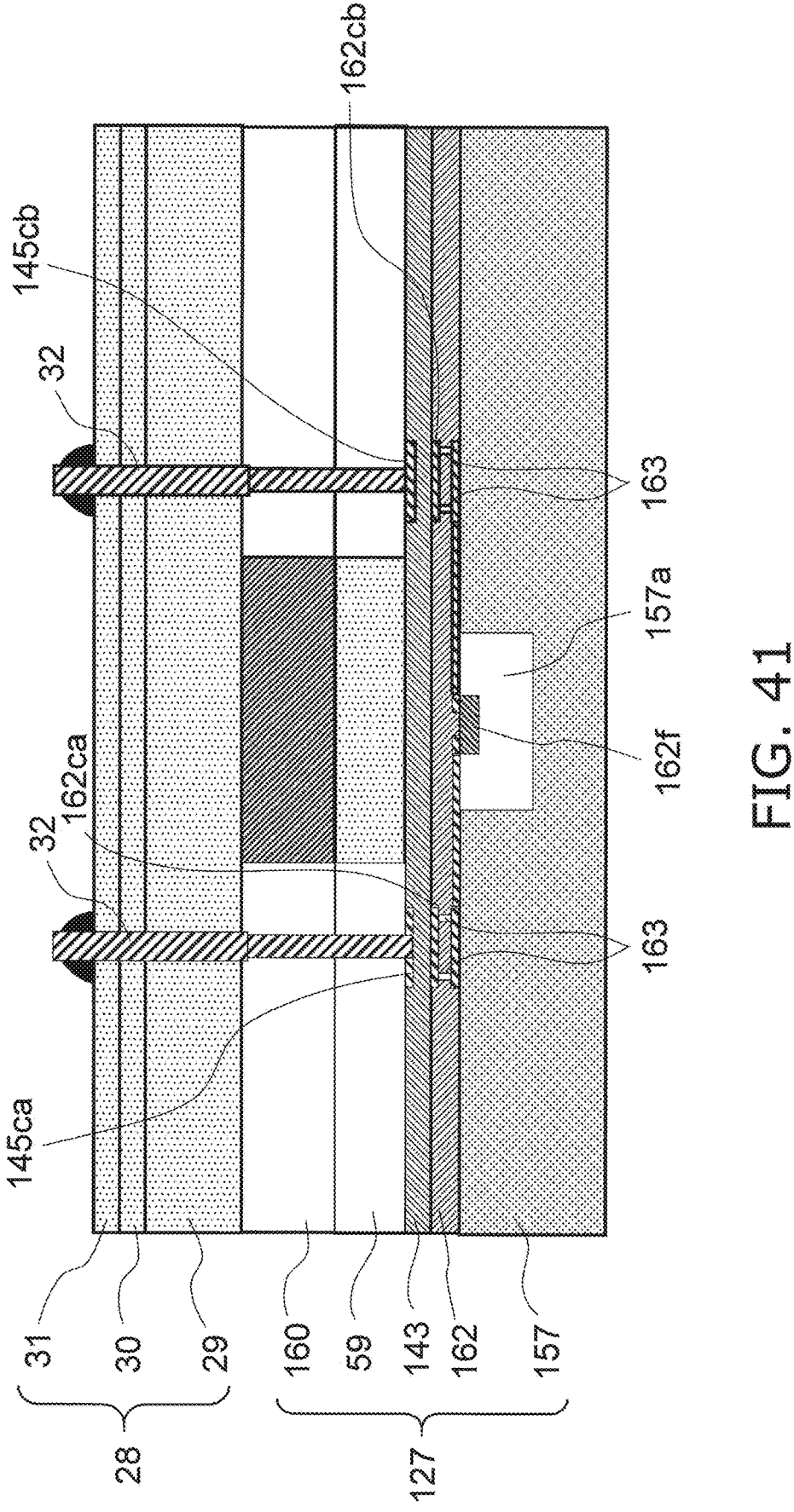
FIG. 41 is a cross-sectional view showing a state in which a board unit is assembled on the upper surface side of the sensor unit in FIG. 40.

FIG. 41 shows a state in which the board unit 28 has been assembled onto the upper surface side of the sensor unit 127 from above.

The connecting portions 32 extending downward from the board 31 pass through the through-holes 176 for the first working electrode and the through-holes 179 for the second working electrode pad, and are electrically connected to the contact portions 145c of the sensors 143 (the first working electrode contact portions 145ca and the second working electrode contact portions 145cb).

This electrical connection structure is the same on the counter electrode pad through-hole 177 side and the reference electrode pad through-hole 178 side.

The gasket sheet 160 of the sensor unit 127 is formed to connect to the additive addition portion A addition port 173, the additive addition portion B addition port 174, the stirring member air discharge suction port 175, and the contact portions 145c of the sensors 143, is disposed so as to cover the peripheries of the first working electrode pad through-hole 176, the counter electrode pad through-hole 177, the reference electrode pad through-hole 178, and the second working electrode pad through-hole 179. Consequently, the gasket sheet 160 servers as both a waterproofing means and a condensation prevention means.

Here, since glass epoxy, which is the material of the heater board 162, has a relatively low thermal conductivity, the heat generated in the resistance heating elements 162f is efficiently transferred to the vias 163, which are formed from a conductive material.

Since the vias 163 are filled with metal plating having high thermal conductivity, the heat generated in the resistance heating elements 162f can be efficiently transferred to the heating electrodes 162ca to 162cd provided on the upper surface side of the heater board 162.

Also, since the vias 163 is filled with metal plating, the upper surface side is flattened and the contact surface area between the heater board 162 and the sensors 143 can be increased. As a result, heat can be efficiently transferred to the contact portions 145c of the sensors 143 provided above the heating electrodes 162ca to 162cd.

Heating the heating electrodes 162ca to 162cd effectively suppresses the occurrence of condensation at the contact portions 145ca to 145cd of the sensors 143 above the heater board 162.

A bottom plate 157 is disposed below the heater board 162.

Since the bottom plate 157 is made of a material with low thermal conductivity (such as ABS, PS, or another such resin material), it has the effect of blocking heat from the heater board 162.

This effectively reduces the effect that heat has on the wells 25a provided below the bottom plate 157.

Furthermore, as shown in FIG. 41, a concave portion 157a is formed in the top surface of the bottom plate 157 so as to surround the resistance heating element 162f.

Consequently, a structure can be obtained with which direct contact between the resistance heating elements 162f and the bottom plate 157 is avoided, while the presence of air, which has low thermal conductivity, in the space formed in the concave portions 157a makes it less likely that the heat from the resistance heating elements 162f will be transmitted to the bottom plate 157.

As a result, by suppressing an increase in the temperature of the bottom plate 157 itself and preventing an increase in the temperature of the atmosphere within the well plate 25 provided below the bottom plate 157, the effect that heat has on the cell culture in the wells 25a can be reduced.

Furthermore, the bottom plate 157 prevents water vapor evaporated from the well plate 25 provided below from flowing into the heater board 162 and the contact portions 145c of the sensors 143 above, so a sensor unit 127 having a function of waterproofing electrical components can be obtained.

OTHER EMBODIMENTS

An embodiment of the present invention was described above, but the present invention is not limited to or by the above embodiment, and various modifications are possible without departing from the gist of the invention.

(A)

In Embodiment 1, an example was given of using the substantially I-shaped sensors 43, but the present invention is not limited to this.

Figure 28:
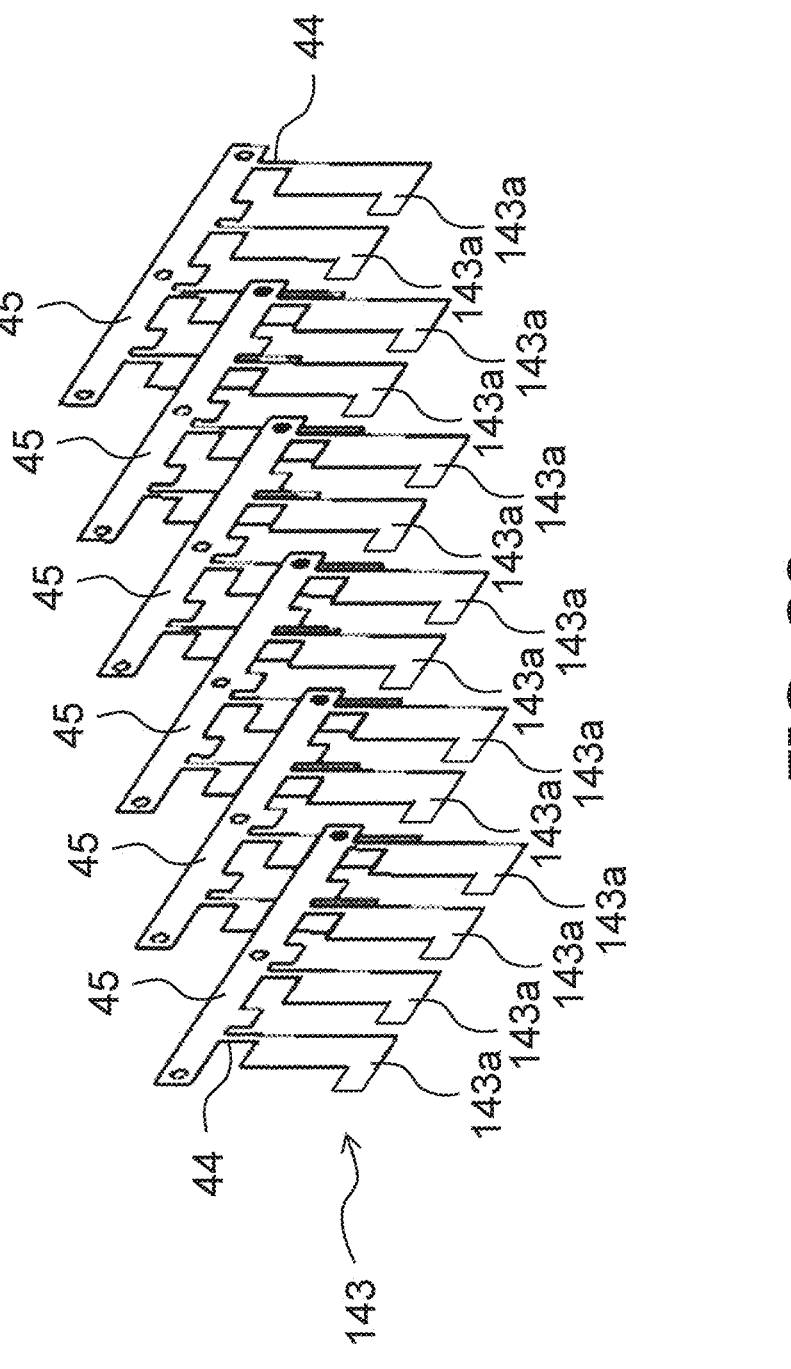
FIG. 28 is an oblique view of the configuration of the sensor included in a sensor unit according to another embodiment of the invention.

For example, as shown in FIG. 28, substantially L-shaped sensors 143 may be used.

As shown in FIG. 28, the sensors 143 have substantially L-shaped main bodies 143a, and just as in Embodiment 1 above, the upper ends of the plurality (four) of sensors 143 are linked by the linking portions 45 via the bending portions 44.

In this case, the surface area of the lower end portions of the sensors 143 immersed in the culture medium (the surface area of the sensing units where the electrodes are disposed) is larger, so the sensing accuracy can be improved over that of the sensors 43 in the above embodiment.

(B)

In Embodiment 1 above, an example was given in which the prongs 57c provided on the bottom plate 57 side and the positioning holes 45b provided on the linking portion 45 side functioned as latching mechanisms for positioning the sensors 43, but the present invention is not limited to this.

For example, contrary to the above embodiment, positioning holes provided on the bottom plate side and prongs provided on the linking portion side may be provided as latching mechanisms.

(C)

In Embodiment 1 above, an example was given in which the sensors 43 were used in a state of having been bent at the bending portions 44. However, the present invention is not limited to this.

For example, the configuration may be such that the sensors are used without being bent.

Here again, the configuration is such that a plurality of sensors are linked by linking portions at the upper end portions of the main bodies of the sensors, which affords the same effect of improving the positional accuracy of the sensors as described above.

(D)

In Embodiment 1 above, an example was given in which the upper end portions of four sensors 43 were linked by a linking portion 45 so that the four sensors 43 formed a set. However, the present invention is not limited to this.

For example, the number of sensors linked by the linking portion may be three or fewer, or may be five or more.

In any case, since the positions between the mutually linked sensors are accurately defined, the positional accuracy of the sensors can be improved.

(E)

In Embodiment 1 above, an example was given in which the linking portion 45 connected four sensors 43 was provided with three positioning holes 45b. However, the present invention is not limited to this.

For example, just like the number of sensors, the number of positioning holes may be two or fewer, or may be four or more.

(F)

In Embodiment 1 above, an example was given in which the sensor fixing jigs 71 and 72 were used in the step of assembling the sensor unit 27. However, the present invention is not limited to this.

For example, the assembly of the sensor unit does not necessarily have to be performed using sensor fixing jigs.

(G)

In Embodiments 2 and 3 above, an example was given of using substantially I-shaped or substantially inverted T-shaped sensors 43. However, the present invention is not limited to this.

For example, the shape of the sensors may be a substantially inverted L shape.

(H)

In Embodiment 2 above, the heating electrodes 62c disposed opposite the contact portions 45c of the sensors 43 heated the contact portions 45c, and this prevented condensation from occurring near the contact portions.

Similarly, in Embodiment 3, the heating electrodes 162ca to 162cd disposed opposite the contact portions 145ca and 145cb for the first and second working electrodes, the contact portions 145cc for the counter electrode, and the contact portions 145cd for the reference electrode in the sensors 143 heated the contact portions 145ca and 145cb for the first and second working electrodes, the contact portions 145cc for the counter electrode, and the contact portions 145cd for the reference electrode, thereby preventing condensation from occurring near the contact portions.

However, the present invention is not limited to this.

For example, the heating units may be configured to heat the periphery of the contact portions, such as the area between the contact portions. That is, the heating units may be configured to heat at least the contact portions or the periphery around the contact portions.

Here again, by heating between the contact portions to prevent condensation in this area, it is possible to avoid the flow of leakage current between the contact portions, which would render the sensors unable to measure.

(I)

In Embodiment 2 above, an example was given in which the four contact portions 45c of a sensor 43 were disposed in a row.

In Embodiment 3 above, an example was given in which the four contact portions 145c of a sensor 143 were disposed at the four corners of a substantially rectangular shape.

However, the invention is not limited to these examples.

For instance, the number of contact portions may be three or fewer, or may be five or more.

Also, the contact portions may be in any layout, rather than being disposed in a row or at the four corners of a substantially rectangular shape.

(J)

In Embodiments 2 and 3 above, an example was given in which the heating electrodes 62c and 162c serving as heating units were disposed on the upper surface (second surface) side of the heater board 62, and the resistance heating elements 62f serving as a heat source were disposed on the lower surface (first surface) (the opposite side) of the heater board 62. However, the present invention is not limited to this.

For example, the heating units and the heat sources may be disposed on the same surface of the heater board, or the heating units may be disposed on the lower surface side and the heat sources on the upper surface side.

(K)

In Embodiments 2 and 3 above, the heat generated in the resistance heating elements 62f and 162f disposed on the lower surface side of the heater boards 62 and 162 was transferred to the upper surface side of the heater boards 62 and 162 through the vias 163 formed in the heating electrodes 62c and 162c. However, the present invention is not limited to this.

For example, when the resistance heating elements serving as heat sources and the heating electrodes are provided on the same surface, a configuration without vias may be used.

Alternatively, heat may be transferred to the surface on the opposite side of the heater board through some heat transfer means other than vias.

(L)

In Embodiments 2 and 3 above, an example was given in which the heating electrodes 62c and 162c that heated the contact portions 45c and 145c were provided to the heater board 62. However, the present invention is not limited to this.

For example, the heating units disposed so as to make contact near the contact portions to be heated may be disposed individually instead of on the board.

(M)

In Embodiments 2 and 3 above, an example was given in which the sensors 43 were used in a state of having been bent at the bending portions 44. However, the present invention is not limited to this.

For example, the configuration may be such that the sensors are used without being bent.

Here again, the same effect of improving the positional accuracy of the sensors can be obtained with a configuration in which a plurality of sensors are linked by a linking portion at the upper end portion of the main bodies of the sensors.

(N)

In Embodiments 2 and 3 above, an example was given in which the upper end portions of four sensors 43 were linked by the linking portion 45 so that the four sensors 43 formed one set. However, the present invention is not limited to this.

For example, the sensors may be used alone, without being linked by a linking portion.

(O)

In Embodiments 2 and 3 above, an example was given in which the well plate 25 including four rows of six wells 25a was used as the culture vessel. However, the present invention is not limited to this.

For example, a well plate in which a plurality of wells are disposed in the desired number, such as three rows of four wells, or two rows of three wells, may be used as the culture vessel.

Alternatively, the device may be such that cell culture is performed by immersing one sensor in one culture vessel.

APPENDICES

Japanese Patent Application Laid-Open No. 2004-113092, for example, discloses a cell culture chip provided with a sensor for sensing the pH, temperature, etc., of the culture solution inside a well in order to monitor the state of a culture medium over an extended period by replacing the culture medium at a appropriate intervals, and to record the process by photography (video) or the like.

With to this cell culture chip, since a sensor is provided for sensing the pH, temperature, etc., of the culture solution in the well, the point at which the culture solution should be replaced can be accurately ascertained.

However, following problem is encountered with the conventional cell culture chip described above.

A cell culture chips is generally used in a hot and humid environment in order to promote cell culture. In this case, if condensation occurs around the electrical contacts, causing a short-circuit between the electrical contacts so that leakage current flows, a stable electrical connection cannot be made, and there is a risk that the cell culture chip may become unusable.

It is an object of the present invention to provide a sensor unit with which stable electrical connection can be ensured by preventing the unit from becoming unusable due to electrical short-circuiting even in a hot and humid environment, as well as a cell culture analysis device equipped with this sensor unit.

The sensor unit according to the present invention has sensors for measuring components of in culture medium in a culture vessel, and comprises sensors and heating units. The sensors each have a main body, a sensing unit that is disposed on the main body and is immersed in the culture medium, and a connection terminal portion that is electrically connected to the sensing unit and measures a component of the culture medium. The heating unit heats at least the connection terminal portion of the sensor, or the periphery thereof.

With the sensor unit of the present invention, stable electrical connection can be ensured by preventing electrical short-circuiting in the unit even in a hot and humid environment.

Appendix 1

A sensor unit having sensors for measuring the components of culture medium in a culture vessel, the sensor unit comprising:

sensors each having a main body, a sensing unit that is disposed on the main body and is immersed in the culture medium, and a connection terminal portion that is electrically connected to the sensing unit and measures a component of the culture medium; and a heating unit that heats at least the connection terminal portion of the sensor, or periphery thereof.

Appendix 2

The sensor unit according to Appendix 1, further comprising:

a board that is provided with the heating units, and which is disposed so that the heating units make contact with the connection terminal portions, or the periphery thereof.

Appendix 3

The sensor unit according to Appendix 2, wherein the board has a first surface and a second surface on an opposite side the first surface, and the heating units each have a heating element provided on a side of the first surface of the board, heating electrodes provided on a side of the second surface, and vias that connect the heating element and the heating electrodes and are disposed so as to make contact near the connection terminal portion of the sensor.

Appendix 4

The sensor unit according to Appendix 3, wherein the connection terminal portion has a first surface and a second surface on the opposite side from the first surface, and a connection terminal is provided on the side of the second surface of the connection terminal portion, and the second surface of the board makes contact with the side of the first surface of the connection terminal portion.

Appendix 5

The sensor unit according to any of Appendices 1 to 4, wherein the connection terminal portion includes a connection terminal portion for the first working electrode and a connection terminal portion for the second working electrode, and the connection terminal portion for the first working electrode and the connection terminal portion for the second working electrode are disposed a specific distance apart.

Appendix 6

The sensor unit according to Appendix 5, wherein the connection terminal portion further includes a connection terminal portion for a counter electrode and a connection terminal portion for a reference electrode, and the distance between the connection terminal portion for the first working electrode and the connection terminal portion for the second working electrode is greater than the distance to the connection terminal portion for the counter electrode, or the distance to the connection terminal portion for the reference electrode.

Appendix 7

The sensor unit according to any of Appendices 1 to 6, wherein the heating unit is a resistance heating element.

Appendix 8

The sensor unit according to any of Appendices 1 to 7, further comprising a connecting portion that is electrically connected to the connection terminal portion and applies voltage to the connection terminal portion.

Appendix 9

The sensor unit according to Appendix 8, wherein the connection terminal portion has a first surface, a second surface on the opposite side from the first surface, and a connection terminal that is disposed on the side of the second surface, and the connecting portion makes contact with the connection terminal disposed on the side of the second surface.

Appendix 10

The sensor unit according to any of Appendices 2 to 4, wherein the board has through-holes into which are inserted the sensors disposed facing substantially vertically downward.

Appendix 11

The sensor unit according to any of Appendices 2 to 4 and 10, wherein the board has a first surface and a second surface on the opposite side from the first surface, further comprising a bottom plate that is provided between the first surface of the board and the culture vessel.

Appendix 12

The sensor unit according to Appendix 11, wherein the bottom plate has a concave portion that is provided on the upper surface of the bottom plate and forms a space surrounding the heating unit.

Appendix 13

The sensor unit according to appendix 8 or 9, wherein the linking portion is a contact probe.

Appendix 14

A cell culture analysis device, comprising:

the sensor unit according to any of Appendixes 1 to 13; and a culture vessel installation portion on which the sensor unit is placed.

Appendix 15

The cell culture analysis device according to appendix 14, further comprising a support body that is provided between the sensor unit and the culture vessel installation portion and forms a housing space in which the culture vessel is installed.

Appendix 16

The cell culture analysis device according to appendix 14 or 15, further comprising a control unit that is disposed on the sensor unit and controls the sensor unit.

The invention claimed is:

1. A sensor unit having sensors for measuring components of culture medium in a culture vessel, the sensor unit comprising:

a plurality of sensors having a main body, which is a flat member, and a sensing unit that is disposed on a lower end side of the main body and is immersed in the culture medium to measure the components of the culture medium;

a linking portion that links the plurality of sensors on an upper end side of the main body; and a bending portion where the plurality of sensors are bent in a thickness direction of the main body such that the linking portion is bent with respect to the main body along a bending line substantially parallel to a lengthwise direction of the linking portion.

2. The sensor unit according to claim 1, further comprising:

a bottom plate provided below the linking portion of the sensors; and a top plate provided above the linking portion of the sensors.

3. The sensor unit according to claim 2, wherein a part of the sensors is positioned to be sandwiched from above and below between the bottom plate and the top plate.

4. The sensor unit according to claim 2, wherein the bottom plate has a plurality of through-holes through which the sensors pass.

5. The sensor unit according to claim 4, wherein the bottom plate further has a support portion that is provided at an opening edge of the through-holes and supports a lower surface side of the bending portion of the sensors, and the top plate has a pressing portion that is provided at a portion opposite the support portion and presses downward on an upper surface side of the bending portion of the sensors.

6. The sensor unit according to claim 5, wherein the support portion has a curved upper surface shape, and the pressing portion has a curved lower surface shape.

7. The sensor unit according to claim 4, wherein the plurality of sensors further have contact portions that are disposed along an extension line of the bending line and make contact with an upper surface of the bottom plate in a state in which the main body of each of the plurality of sensors has been inserted into the plurality of through-holes.

8. The sensor unit according to claim 4, further comprising a latching mechanism configured to latch the linking portion bent along the bending line of the bending portion to an upper surface of the bottom plate.

9. The sensor unit according to claim 8, wherein the latching mechanism has a positioning hole formed in the linking portion, and a prong that is provided to the upper surface of the bottom plate and is inserted into the positioning hole to hold the linking portion.

10. The sensor unit according to claim 9, wherein the prong has a holding surface that holds a surface of the linking portion, which is bent along the bending line, along the upper surface of the bottom plate.

11. The sensor unit according to claim 4, wherein the bending portion is narrower in width than the main body.

12. The sensor unit according to claim 4, wherein the through-holes in the bottom plate have an insertion portion that is wider than the sensor and into which the sensor is inserted, and a holding part that is narrower than the insertion portion and in which the sensor inserted into the insertion portion is held while moving substantially parallel to an upper surface of the bottom plate.

13. The sensor unit according to claim 1, wherein the sensor is approximately I shaped.

14. The sensor unit according to claim 1, wherein the sensor is substantially L shaped.

15. A cell culture analysis device, comprising:

the sensor unit according to claim 1; and a culture vessel installation portion on which the sensor
  unit is placed.

16. The cell culture analysis device according to claim 15,
further comprising a control unit that is disposed on the
  sensor unit and is configured to control the sensor unit.

17. The sensor unit according to claim 1, wherein the linking portion comprises one of a plurality of linking
  portions respectively formed in each of the plurality of
  sensors, at least two of the plurality of linking portions have
  principal surfaces facing in the same direction, and the bending line is drawn on each of the principal surfaces
  such that the principal surface is bent toward a front
  side or a rear side of the principal surface.

* * * * *